(12) United States Patent
Sontheimer et al.

(10) Patent No.: US 6,303,339 B1
(45) Date of Patent: Oct. 16, 2001

(54) DNA SEGMENTS ENCODING AUTOIMMUNE POLYPEPTIDE EPITOPES OF RO/SS-A ANTIGEN

(75) Inventors: Richard D. Sontheimer, Carrollton; Tsu-San Lieu, Dallas; Daniel P. McCauliffe, Farmers Branch; J. Donald Capra, Dallas, all of TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 07/576,423

(22) PCT Filed: Mar. 22, 1989

(86) PCT No.: PCT/US89/01213

§ 371 Date: May 24, 1991

§ 102(e) Date: May 24, 1991

Related U.S. Application Data

(63) Continuation-in-part of application No. 07/171,631, filed on Mar. 22, 1988, now abandoned.

(51) Int. Cl.[7] ............ C12P 21/04; C12N 15/09; C12N 15/00; C12Q 1/68
(52) U.S. Cl. ............. 435/69.3; 435/6; 435/7.1; 435/71.1; 435/320.1; 530/403; 536/23.5; 935/77; 935/78; 935/79
(58) Field of Search ............ 435/71.1, 6, 320.1, 435/69.3; 530/403; 536/23.5; 935/77–79

(56) References Cited

U.S. PATENT DOCUMENTS 4,784,942  11/1988  Harley.

OTHER PUBLICATIONS

Deutscher, S.L. et al. Molecular Biology Reports 12:242 1987.*
M. Grunstein et al. Proc. Nat. Acad. Sci 72:3961–5 10/75.*
E.M. Southern. J. Mol. Biol. 98:503–17 1975.*
R.A. Young et al. Proc. Natl. Acad. Sci. 80:1194–8 3/83.*
Reichlin (1980), *Clin. Exp. Immunol.*, 44:1–10.
Lerner et al. (1981), *Science*, pp. 400–402.
Hopp et al. (1981), *Proc. Natl. Acad. Sci., U.S.A.*, 78:3829–3828.
Hendrick et al. (1981), *Mol. Cell. Biol.*, 1:1138–1149.
Yamagata et al. (1984), *J. Clin. Invest.*, 74:625–633.
Lieu et al. (1984)Jrnl. Immunol. Meth., 71:217–228.
Wolin et al. (1984), *Proc. Natl. Acad. Sci., USA*, 81:1996–2000.
Chambers et al. (1985), *Proc. Natl. Acad. Sci., USA*, 82:2115–2119.
Reichlin (1986), *Jrnl. Clin. Immunol.*, 6:339–348.
Whittingham et al. (1987), *The Lancet*, Jul. 4, 1987, pp. 1–3.
Riechlin et al. (1987), *Jrnl. Rheumatol.*, 14:112–117.
Gaither et al. (1987), *J. Clin. Invest*, 79:841–846.
Sontheimer (1988), "The Fine Specificity of Rheumatic Disease Associated Autoantibodies", Medicine Grand Rounds.
Lieu et al. (1987), *Clin. Res.*, 35:388A.
Lieu et al. (1988), American Federation of Clinical Research, Clin. Res., 377a.
Lieu et al. (1988), Society for Investigative Dermatology, Inc., *Clin. Res.*, 668a.

* cited by examiner

*Primary Examiner*—Gary L. Kunz
*Assistant Examiner*—Robert S. Landsman
(74) *Attorney, Agent, or Firm*—Fulbright & Jaworski LLP

(57) ABSTRACT

The present disclosure relates to DNA sequences encoding one or more antigenic epitopes of the Ro 60 kD autoantigen, as well as to antigenic peptides themselves which correspond antigenically to epitopes found on the Ro/SS-A ribonucleoprotein (RNP) particle. Peptides which incorporate the antigenic epitopic core sequences disclosed herein may be employed in place of the Ro/SS-A RNP in any of a variety of immunoassays including ELISA assays. The polypeptides of the invention may be employed in colorimetric assays for the identification and characterization of autoimmune diseases such as systemic lupus erythematosus (SLE) and Sjogren's syndrome. The DNA sequences disclosed herein may be employed in the preparation of the 60 kD Ro antigen, peptides which incorporate antigenic core sequences thereof, to probe for Ro sequences by hybridization analysis, and the like.

15 Claims, 11 Drawing Sheets

1Kb    R = Eco RI    B = Bam HI
       H = Hind III  N = Nco I
       L = Bgl II    P = Pvu II

```
                                      M  L  L  S  V  P  L  L  L  G  L  L    12
ccgtactgcagagccgctgccgaggtcgttttaaagggccgttgccgccccctcggccgccatgctgctatccgtgccgctgctgctcggcctcc   100

G  L  A  V  A  E  P  A  V  Y  F  K  E  Q  F  L  D  G  D  V  T  S  R  W  I  E  S  K  H  K  S  D    45
tggcctggcgtcgccgagccgcgtcgtctacttcaaggagcagtttctggacggagacggtgacttcccgctggatcgaatcaaacacaagtcaga   200

F  G  K  F  V  L  S  S  G  K  F  Y  G  D  E  E  K  D  K  G  L  Q  T  S  Q  D  A  R  F  Y  A  L  S    78
ttttggcaaattcgttctcagttctccggcaagttctacggtgacgaggagaaagataaaggtttgcagacaagccaggatgcacgcttttatgctctgtcg   300

A  S  F  E  P  P  F  S  N  K  G  Q  T  L  V  V  Q  F  T  V  K  H  E  Q  N  I  D  C  G  G  Y  V  K  L   112
gccagtttcgagccttttcagcaacaaaggccagacgctggtggtgcagttcacggtgaaacatgagcagaacatcgactgtgggggcggctatgtgaagc   400

F  P  N  S  L  D  Q  T  D  M  H  G  D  S  E  Y  N  I  M  F  G  P  D  I  C  G  P  G  T  K  K  V  H   145
tgtttcctaatagtttggaccagacagacatgcacggagactcagaatacaacatcatgtttggtccgacatctgtggccctggccaagaaggttca   500

V  I  F  N  Y  K  G  K  N  V  L  I  N  K  D  I  R  C  K  D  D  E  F  T  H  L  Y  T  L  I  V  R  P   178
tgtctatcttcaactacaagggcaagaacgtgctgatcaacaaggacatccgttgcaaggatgatgagttttacacacctgtacacactgattgtgcggcca   600

D  N  T  Y  E  V  K  I  D  N  S  Q  V  E  S  G  S  L  E  D  D  W  D  F  L  P  P  K  K  I  K  D  P  D   212
gacaacacctatgaggtgaagattgacaacagccagqtggagtccggctccttggaagacgattggactccttgccaccaaqaaqataaaqqatcctg   700

A  S  K  P  E  D  W  D  E  R  A  K  I  D  D  P  T  D  S  K  P  E  D  W  D  K  P  E  H  I  P  D  P   245
atgcttcaaaaccggaagccggagqactggqacgaqcqqqccaagatcgatqatcccacagactccaaqcctqaqqactqqqacaaqcccgaqcatatccctqaccc   800

D  A  K  K  P  E  D  W  D  E  E  M  D  G  E  W  E  P  P  V  I  Q  N  P  E  Y  K  G  E  W  K  P  R   278
tgatgctaagaagcccgaggactgqgacgaqqaqatqqacqqaqaqtqqqaaccccaqtqattcaqaaccctqaqtacaaqqqtqaqtqqaaqcccqq   900
```

Fig. 2AA

```
                          M   L   L   S   V   P   L   L   L   G   L   L                    12
ccctcgg cccgccatgctgctatccgtgccgctgctgctcggcctcc                                           100
G   D   G   W   T   S   R   W   I   E   S   K   H   K   S   D                              45
ggagacgggtggacgtcccgctggaatccaaacacaagtcaga                                                200
K   G   L   Q   T   S   Q   D   A   R   F   Y   A   L   S                                   78
ataagggtttgcagacaagccaggatgcacgcttttatgtctgtcg                                             300
V   K   H   E   Q   N   I   D   C   G   G   Y   V   K   L                                  112
ggtgaacaggacagaacatcgactgtggggcggctatgtgaaagc                                              400
I   M   F   G   P   D   I   C   G   P   G   T   K   K   V   H                               145
atcatgtttggtcccgacatctgtggccctggcaccaagaaggttca                                            500
K   D   D   E   F   T   H   L   Y   T   L   I   V   R   P   D                               178
gcaaggatgagttt acacacctgtacacactgattgtgcggcca                                              600
E   D   W   D   F   L   P   P   K   K   I   K   D   P   D                                   212
ggaagacgattgggacttcctgcacccaagaagataaaggatcctg                                             700
D   S   K   P   E   D   W   D   K   P   E   H   I   P   D   P                               245
gactccaagcctgaggactgggacaagcccgagcatatccctgaccc                                            800
P   V   I   Q   N   P   E   Y   K   G   E   W   K   P   R                                   278
cccagtgattcagaaccctgagtacaagggtgagtggaagcccgg                                              900
```

```
  P  E  Y  S  P  D  P  S  I  Y  A  Y  D  N  F  G                     312
ccc gag tat tct ccc gat ccc cag tat cta tgc cta tga taa ctt tg      1000
     L  I  T  N  D  E  A  Y  A  E  F  G  N  E                       345
tcc tca cac cca gat gag gca tac gct gag gtt tgg caa cga             1100
     Q  R  L  K  K  E  D  K  R  K                                    378
gag cag agg ctt aag aca aag gag gac aaa cga aaa                     1200
     E  D  K  E  E  E  D  E  D  K  V  P  G  Q                        412
gag gat aag gag gag gag gat gag gat aag gtc ccc ggc                 1300
                                                 417
gat gag gaa caa tga aga ata cac ccc gcg ccc ttg cca gct tgt gag     1400
ttt gtt ttg ttt ttc ctt ctt cac cct ctc ttc tcc ttt ctt gag         1500
cct ggt cat tct cat tca gat tcc acc tga tcc tgc ctg cct ctg tgc     1600
gcc aca cag ggg cag gat ttc atc ctc atc ttc aac tgc tgg agc cag     1700
ggc ctc ttc att cat tca caa att tta aat tat tct att aat ttt        1800
aga act aca aac aaa t                                               1890
```

DNA SEGMENTS ENCODING AUTOIMMUNE POLYPEPTIDE EPITOPES OF RO/SS-A ANTIGEN

This application is a 371 of PCT/US89/01213, filed Mar. 22, 1989, which is a CIP of 07/171,631, filed Mar. 22, 1988, now abandoned.

The Government may own certain rights in the present invention pursuant to NIH grants 12127, AR19101, AR07341 and/or AR01784.

BACKGROUND OF THE INVENTION

1. Field of the Invention

The present invention relates generally to peptides bearing selected antigenic epitopes and to nucleic acid compositions which may be employed in the preparation of such peptides, or to detect the presence of complementary nucleic acid sequences in biological samples. More particularly, the invention concerns peptides bearing antigenic epitopes corresponding to epitopes on the 60 kD polypeptide of the Ro/SS-A antigen (also referred to simply as the "Ro" antigen), and to DNA sequences encoding all or a portion of the 60 kD polypeptide. The invention further relates to processes incorporating the foregoing peptides and/or nucleic acid sequences, such as in the immunocharacterization of various autoimmune diseases or in the preparation of recombinant Ro antigen.

2. Description of the Related Art

Patients with rheumatic diseases can make autoantibodies to a variety of biological compounds derived from their own cells, including autoantibodies to products secreted by cells (e.g., rheumatoid factor to immuno-globulins), constituents of the plasma membrane (e.g., phospholipids, insulin receptors) as well as an array of intracellular components. Interestingly, of the greater than 10,000 macromolecules found inside a cell, only about 30 are targets of autoantibody production (1). However, autoimmune antibodies having immunospecificity for one or more of these targets are found in a wide array of rheumatic diseases, including systemic lupus erythematosus (SLE), mixed connective tissue disease (MCTD), primary sicca syndrome, polymyositis, dermatomyositis, progressive systemic sclerosis (PSS), rheumatoid arthritis (RA), idiopathic thrombocytopenic purpura (ITP), primary biliary cirrhosis (PBC), chronic active hepatitis (CAH), and a variety of others.

Accordingly, the presence of autoantibodies in the serum of a patient is generally indicative of one or another of the various foregoing conditions. For example, autoantibodies to double-stranded (ds) DNA occur in 50–70% of SLE patients and are highly specific for this disease (2). This autoantibody is also occasionally seen in clinical settings where SLE overlaps with other rheumatic diseases (e.g., mixed connective tissue disease). Moreover, circulating ds-DNA antibody levels fluctuate with systemic disease activity, particularly renal involvement (3–4), and this autoantibody specificity has been implicated in the more aggressive forms of lupus nephritis (5–6).

The presence of one or more of a variety of other autoantibodies have been used as indicators of rheumatic disease, including antibodies having specificity for chromatin structural proteins such as histones or nucleosomal structures or antibodies to ribonucleoprotein particles (RNP) such as nRNP, U1 snRNP and Sm antigens. For example, studies employing solid phase immunoassays have shown that anti-histone antibodies can be found in about 50% of the sera of unselected SLE patients (7–9), and in approximately 80% of patients with active disease (9).

The appearance of antibodies to Ro/SS-A and La/SS-B RNPs were probably first detected in 1958 in the search of patients with Sjogren's Syndrome, employing extracts of salivary tissue as antigens (10). Later studies demonstrated two major specificities in salivary tissue designated SjD and Sjt (11), probably corresponding to Ro/SS-A and La/SS-B, respectively. Reichlin and Harley have offered several recent comprehensive reviews of the clinical correlations of the Ro/SS-A and La/SS-B antigen-antibody systems (12–13).

Most interest has centered on the Ro/SS-A system since an autoantibody response to this antigen is much more common than one to La/SS-B. In addition, an autoantibody response to La/SS-B is almost invariably associated with anti-Ro/SS-A antibody production. Anti-Ro/SS-A autoantibodies occur in the highest prevalence in Sjogren's syndrome (SS) patients. Moreover, some investigators have suggested that the use of a sufficiently sensitive solid phase assay employing purified Ro/SS-A antigen, virtually all SS patients produce this autoantibody (14).

Unfortunately, although purified Ro/SS-A antigen can be employed to immunodiagnose various autoimmune disorders and particularly Sjogren's syndrome, there are significant problems associated with its use. Of principal importance is the fact that although Ro/SS-A RNP particles can be isolated to some degree of purity (15), to do so is economically impractical. This is due principally to the high cost and time of isolating Ro/SS-A antigen proteins from natural sources. Moreover, in that the Ro/SS-A antigen is an RNP particle, it generally has stricter requirements for storage, as well as a more limited ability to prepare for commercial distribution. While a recombinant version of one or more protein subcomponents would prove to be useful in this regard, their development has not been deported. Clearly there is a need for such a recombinant version, including a need for DNA segments which can be employed in the preparation of peptides containing Ro antigenic sequences, which would provide a means for producing improved antigenic materials which may be recognized by antisera having specificity for autoimmune antigens such as Ro/SS-A.

SUMMARY OF THE INVENTION

Accordingly, the invention concerns methods and compositions which may be employed to prepare an improved autoimmune antigenic material that addresses at least some of the disadvantages in the art.

The invention further concerns antigenic material that may be employed in the immunoidentification of autoimmune diseases, and particularly autoimmune diseases such as Sjogren's syndrome, lupus erythematosus and similar or related disorders.

More particularly, the Invention concerns relatively small peptides which may be substituted for RNP antigens such as Ro/SS-A in immunoassays, yet which may be readily prepared synthetically, and easily stored for extended periods of time.

The present invention addresses these concerns in certain embodiments through the provision of DNA sequences which encode antigenic epitopes, referred to herein as epitopic core sequences, of the 60 kD Ro antigen peptide, or biologically functional equivalents thereof. Most conveniently, one will desire to employ the 60 kD Ro antigen-encoding sequences of the invention to produce essentially the complete, natural 60 kD protein by recombinant means. However, for certain applications, the preparation of shorter transcriptional units encoding epitopic core sequence(s) might prove desirable. Therefore, as used herein, the phrase "60 kD antigen", and variations thereof, is intended to refer generally to proteins and peptides bearing the antigenic sequences, including epitopic core sequences, as set forth in the present disclosure. It is specifically pointed out that the use of "60 kD" designation is intended as a reference to the natural 60 kD Ro antigen as a shorthand means or "coined" term for referring to the subject matter of the invention, and is not in any way intended to set forth or imply that the invention is limited to the preparation of proteins exhibiting this particular molecular weight.

This aspect of the invention arises out of the inventors successful cloning of DNA encoding the 60 kD Ro antigen. From knowledge of this 60 kD Ro antigen DNA sequence as disclosed herein, one is enabled to prepare DNA sequences which encode a peptide which include at least an epitopic core sequence of the 60 kD Ro antigen, or which encode the full length antigen itself. Moreover, from knowledge of the biological interchangeability of various amino acids which allow one to alter amino acid structures without altering their underlying their biological functional activity, one is enabled by the present disclosure to prepare a wide range of equivalent embodiments, so called biologically functional equivalents as discussed below.

The invention is thus concerned in particular aspects with DNA sequences which encode the 60 kD Ro antigen identified as having an amino acid sequence essentially as set forth in FIG. 2. This 60 kD Ro antigen is one of two Ro antigens found to have a molecular weight of about 60 kD when subjected to SDS-polyacrylamide gel electrophoresis. The 60 kD Ro antigen of the present invention has been found to contain epitopic core sequences which can be used in the preparation of proteins and peptides, useful in the immunological detection and identification of various autoimmune diseases, including disease such as systemic lupus erythematosus (SLE) and Sjogren's syndrome. The 60 kD Ro antigen, or antigenic peptides containing 60 kD Ro antigen epitopes, can thus be employed directly in immunoassays such as those designed to detect the presence of cross-reacting antibodies in clinical samples.

Sequence information obtained for the 60 kD protein and disclosed herein, whether it be amino acid or nucleic acid sequence information, can be used to construct synthetic peptides in accordance with the invention. This can be achieved either by chemical synthesis means, such as peptide synthesis, or through the use of recombinant techniques, for example, through the construction of recombinant hosts which express proteins or peptides in accordance with the invention. Thus, through information provided herein, one can construct DNA sequences which encode epitopic core sequences derived from the 60 kD Ro antigen, or one can construct such antigens directly. In any event, nucleic acid sequences encoding the 60 kD Ro antigen, or epitopic core sequences therefrom, are important aspects of the present invention.

Where recombinant techniques are employed to produce peptides in accordance with the invention, it will be appreciated by those of skill in the art in light of the present disclosure that it may be advantageous to prepare recombinant vectors, such as plasmids, bacteriophage, viruses, etc., which incorporate recombinant DNA sequences encoding the desired amino acid sequences. The preparation and use of such vectors which incorporate the appropriate recombinant DNA segments will be apparent to those of skill in light of the disclosure herein and in light of techniques well known in the art. As used herein, the term "recombinant DNA segment" or "insert" means any DNA segment or fragment that is inserted into a recombinant vector either for the purpose of replicating or for expressing the recombinant fragment in a recombinant host to produce a desired peptide.

The preparation and use of recombinant DNA segments in the practice of the invention offers many advantages, including among others, the ability to construct DNA segments which encode peptides having sequences which generally correspond to Ro antigen sequences as disclosed herein, yet which has one or more sequence modifications. This is referred to in the art generally as the ability to prepare so-called "second generation" structures. The sequence characterization of the 60 kD Ro antigen provided herein enables the preparation of such second generation structures, e.g., through the practice of specific DNA mutagenesis techniques, which are now well known in the art.

Of course, where one desires to prepare and isolate DNA segments which encode the 60 kD antigen, or antigenic subportions thereof, the nucleic acid sequence of FIG. 2 will find particular utility in the preparation of nucleic acid hybridization probes. Such probes are useful in the identification and selection of recombinant clones bearing the desired sequences. In that to be useful, hybridization probes must be of sufficient length so as to be able to form a relatively stable hybrid duplex with the target nucleic acid, one will desire to prepare probes having a length that is chosen to maximize duplex stability. It is generally believed that such probes, whether DNA or RNA in nature, should be at least about 14 or so nucleotides in length, and more preferably about 18, or even 22 or so nucleotides in length. Such minimum probe lengths are preferred in order to ensure stable duplex formation under the selected hybridization conditions, as well as to minimize the possibility of cross hybridization to unrelated sequences. As will be appreciated, preferred hybridization conditions for such purposes will generally be more stringent conditions such as hybridization in about 6×SSC at about 42° C. for about 18 or so hours, followed by washing with 1×SSC for 2 hours at 42° C., depending on the probe or primer length being used. These conditions serve to minimize undesirable cross- and non-specific hybridization.

Accordingly, for embodiments directed to the preparation and use of nucleic acid segments such as the foregoing, the invention may be defined in particular aspects as being directed to substantially purified nucleic acid segments which correspond, or are complementary to, at least a 14 nucleotide long region of the DNA sequence of FIG. 2. In more preferred aspects, such segments may be defined as corresponding to, or being complementary to, at least an 18, or even 22, nucleotide long region of the DNA sequence of FIG. 2. As used herein, the term "substantially purified" is intended to refer to DNA segments isolated free of their natural state as they may be present in the genome of an organism, and is intended to include such segments as they would exist, e.g., upon genetic engineering such as by insertion into a recombinant vector.

The invention is directed in certain embodiments to a method for identifying the presence of a nucleic acid sequence which encodes at least a portion of the 60 kD Ro antigen, or a biologically functional equivalent thereof, in a biological sample suspected of containing such a sequence. The method of this aspect of the invention involves generally the steps of 1) incubating nucleic acids which may be present in the biological sample with a 60 kD Ro antigen DNA segment disclosed herein under conditions appropriate for the formation of specific hybrids; and 2) detecting the formation of specific hybrids between the nucleic acids and the segment by means of a label, wherein the formation of such a duplex is indicative of the presence of such a nucleic acid sequence in the biological sample. The term "biological sample" is thus intended to refer broadly to any sample containing, or thought to contain, biological genetic material, and includes, e.g., a recombinant host cell colony or even isolated DNA samples.

Antigens of the invention may be defined as including polypeptides of a relatively short length, which cross-react immunologically with antisera reactive against the 60 KD protein of the Ro/SS-A antigen. Such polypeptides have been shown by the inventors to be useful in the identification of the anti-Ro/SS-A antibodies in clinical samples, and it is proposed generally that the polypeptides described herein will prove useful in the same ways that one may employ the Ro/SS-A antigen itself, for example, in a variety of immunological techniques including both competitive and non-competitive immunoassays.

The present invention is accordingly directed in particular embodiments to peptides which incorporate amino acid sequences discovered by the inventors to correspond to antigenic epitope(s) of the Ro/SS-A antigen. An aspect of the invention is predicated at least in part on a realization by the inventors that a simple peptide sequence can be employed, e.g., in immunoassays, in place of the natural Ro/SS-A ribonucleoprotein complex itself.

As noted above, certain embodiments of the invention relate to DNA sequences which encode antigenic sequences of amino acids that include within their sequence an epitopic "core" sequence, as well as to the antigenic peptides themselves. An epitopic core sequence, as used herein, is a relatively short stretch of amino acids that is "complementary" to, and therefore will bind, antigen binding sites on anti-Ro antibodies (i.e., anti-Ro/SS-A antibodies). It will be understood that in the context of the present disclosure, the term "complementary", when used in connection with amino acid sequences, refers to amino acids or peptides that exhibit an attractive force towards each other. Thus, epitope core sequences of the present invention may be operationally defined in terms of their ability to compete with or even displace the binding of Ro/SS-A antigen with anti-Ro/SS-A antisera. With respect to nucleic acid sequences, the term "complementary" sequences refers to sequences having sufficient complimentarily to allow specific cross-hybridization of nucleic acid strands.

The size of the encoded polypeptide antigen is not believed to be particularly crucial, so long as it is at least large enough to carry the identified epitope core sequence or sequences. The smallest core sequence of the present disclosure is on the order of about 13 amino acids in length. Thus, this size will generally correspond to the smallest peptide antigens prepared in accordance with the invention, of course, the size of the antigen may be larger where desired, so long as it contains the basic epitopic core sequence.

Certain embodiments of the invention are directed to the recombinant production of RO antigenic proteins or peptides. In general, these embodiments concern methods for the preparation of a peptide which includes at least an epitopic core sequence of the 60 kD Ro antigen, or a biologically functional equivalent thereof. These methods include generally 1) preparing a recombinant vector which incorporates the desired Ro antigen-encoding DNA sequence; 2) translationally expressing the recombinant vector in an appropriate host so as to obtain expression of the Ro antigen-encoding sequences; and 3) collecting the peptide so produced.

In certain embodiments, antigens of the invention may be defined in terms of polypeptides which include within their sequence the following sequence of amino acids discovered by the present inventors to comprise a Ro/SS-A epitopic core sequence:

-lys-glu-gln-phe-leu-asp-gly-asp-gly-trp-thr-asp/ser-arg- (see FIG. 2, amino acids 24 to 36);

-asn-ser-gln-val-glu-ser-gly-ser-leu-glu-asp-asp-trp-asp-phe-leu-pro-pro-lys-lys-ile-lys— (amino acids 188 to 209); and -his-ile-pro-asp-pro-asp-ala-lys-lys-pro-glu-asp-trp-asp-glu- (amino acids 241–255). or biologically functional equivalent amino acids. [As an example of biological functional equivalents, experimentation has indicated to the inventors that the amino acid at position 12 (FIG. 2 amino acid no. 35) of the first of the foregoing epitopic core sequence can be either an "asp" or "ser" residues.]

As noted, these polypeptides will typically have an overall length ranging from about 13 to about 25 amino acids. Thus, the lower size limit for the peptide will correspond to about the size of the epitope itself, about 13 amino acids, whereas the upper size of the peptide antigen will be about 25. Peptides much larger than this are generally undesirable for a variety of reasons, including, e.g., added difficulty in synthesis (if synthesized), changes is solubility properties, or inadvertent addition of undesirable epitopes.

In more preferred embodiments, the peptide antigen will be selected from the group of peptides consisting essentially of:

-phe-lys-glu-gln-phe-leu-asp-gly-asp-gly-trp-thr-asp/ser-arg-;

-lys-glu-gln-phe-leu-asp-gly-asp-gly-trp-thr-asp/ser-arg-trp-ile-glu-ser-;

-asn-ser-gln-val-glu-ser-gly-ser-leu-glu-asp-asp-trp-asp-phe-leu-pro-pro-lys-lys-ile-lys-;

-his-ile-pro-asp-pro-asp-ala-lys-lys-pro-glu-asp-trp-asp-glu-; or biologically functional equivalent amino acids, or larger peptides which incorporate these sequences or their functional equivalents. As will be appreciated, the foregoing sequences include within their sequences the basic epitopic core sequences discussed above.

As used herein, the phrase "biologically functional equivalent" amino acids refers to the fact that the invention contemplates that changes may be made in certain of the foregoing basic amino acid sequence(s), without necessarily reducing or losing their antigenic identity. For example, the sequence can be altered through considerations based on similarity in charge (e.g., acidity or basicity of the amino acid side group), hydropathic index, or amphipathic score. In general, these broader aspects of the invention are founded in part on the foregoing general understanding in the art that certain amino acids may be substituted for other like amino acids without appreciable loss of the peptide's ability to bind to the antibodies, and thus be recognized antigenically. Exemplary amino acid substitutions are set forth hereinbelow.

In exemplary embodiments, it is proposed that biologically functional equivalents of one of the foregoing epitopic core sequences can be identified by the formula:

$$-[AA]-$$
$$1-13$$

wherein,

AA$_1$=lys, arg, gln, or asn;
AA$_2$=glu, asp, gln, or asn;
AA$_3$=gln, asn, arg, or asp;
AA$_4$=phe, tyr, or trp;
AA$_5$=leu, ile, or val;
AA$_6$=asp, glu, asn, or gln:
AA$_7$=gly, ala, or thr;
AA$_8$=asp, glu, asn, or gln;
AA$_9$=gly, ala, or thr;
AA$_{10}$=trp, tyr, or phe;
AA$_{11}$=thr, ser, or gly;
AA$_{12}$=asp, glu, asn, gln, ser, thr, ala or gly;
AA$_{13}$=arg, lys, asn, or gln.

The foregoing exemplary embodiment demonstrates possible biologically functional equivalents of the 13 amino acid long epitopic core sequence discussed above. It should be appreciated that the present invention contemplates that similar types of substitutions will prove useful in preparing biologically functional equivalents of the remaining epitopic core sequences set forth herein.

As noted above, certain aspects of the invention relate to DNA or nucleic acid sequences encoding antigenic peptides which incorporate antigenic core sequences such as the foregoing. A particular embodiment of the invention thus relates to DNA or nucleic acid segments which encode one or more of the epitopic core peptide sequences set forth in FIG. 2. One such DNA segment encodes amino acids 23 or 24 through 36 of the amino acid sequence of FIG. 2. Another such segment useful in the practice of the invention encodes amino acids 23 or 24 through 40 of the amino acid sequence of FIG. 2. Still another such segment encodes amino acids 188 through 209. These regions of the 60 kD Ro antigen of FIG. 2 correspond to the epitopic core sequences discussed above.

In addition to the foregoing sequences, it is believed that the Ro antigen of FIG. 2 includes numerous other potential antigenic core sequences which may be similarly employed in the practice of the invention. Such antigenic core sequences can be identified as relatively hydrophilic stretches of amino acids along the FIG. 2 amino acid sequence, and may be predicted, for example, through the use of software designed to predict antigenic amino acid structures. Software, such as Chou-fasman, has been employed by the inventors to identify antigenic regions of peptides by means of a consideration of the hydrophobicity and/or hydrophilicity of peptidyl structures. From such an analysis of the FIG. 2 antigen, at least 3 or so regions have been identified as likely containing antigenic core sequences. These regions, as denoted in FIG. 2, correspond generally to amino acids 24 through 36; amino acids 188 through 209; and amino acids 241 through 255. Therefore, in certain aspects, the invention is concerned with nucleic acids which encode the foregoing core sequences, as well as the peptides themselves.

Of course, the antigenic peptides of the invention will generally find their greatest utility in assays which require the selection and/or identification of antibodies having reactivity with Ro/SS-A RNP antigens, such as in the context of ELISAs, RIAs, or even Western blot analyses. In a general sense, these immunologic methods include methods for testing for the presence of anti-Ro/SS-A antibodies in a sample, comprising immunologically testing the sample for antibodies which cross react with an antigen which includes within its amino acid sequence one or more of the foregoing Ro/SS-A epitopic core sequences.

For example, in the context of an ELISA assay for detecting anti-Ro/SS-A antibodies (or antigens) in a sample (e.g., a clinical sample which contains antibodies), antigens of the present invention may be employed in a number of manners. In so-called non-competitive assays, antigens in accordance with the invention may be employed directly to identify cross-reacting antisera by, e.g., binding Ro/SS-A epitopic core sequence-containing peptides to a solid matrix, contacting the surface with the antibody-containing sample under conditions which are favorable to immunocomplex formation, washing to remove non-immunocomplexed material, and detecting any such immunocomplex formation.

Use of antigenic peptides of the invention in the context of competitive assays such as RIAs or competitive ELISAs is similarly enabled. In these assays, the Ro/SS-A epitope-containing peptides may be employed to identify either Ro/SS-A antigen or its corresponding antibody. For example, standard curves can be determined experimentally which plot the correlation between the concentration of Ro/SS-A epitopic core peptides and immunoreactivity with anti-Ro/SS-A antisera. By introducing unknown quantities of antigenic material into the quantified immunoreaction, for example, from a clinical sample, one can calculate the amount of antigen contained therein by the ability of the clinical sample to "compete" with the control.

Accordingly, particular advantages of the invention will be realized through the preparation of synthetic peptides which include the desired epitopic core sequences. As used herein, the term "synthetic" peptides or antigens refers to peptides or antigens which are prepared by means other than by purification of naturally occurring peptides or compositions. Thus, "synthetic" peptides includes protein sequences prepared by peptide synthesis or through recombinant production. Thus, the invention is directed in a broad sense to synthetic peptides which include the above-described epitopic core sequences, or their biological functional equivalents, within their structures. As will be appreciated by those who practice the present invention, the use of these so-called "synthetic" peptides in place of naturally occurring antigens will result in a number of distinct advantages which are not enabled by use of the naturally occurring Ro/SS-A RNP antigen.

Further, it is pointed out that the invention is directed in certain embodiments to immunodetection kits for detecting Ro/SS-A antigens or antibodies in samples. Such kits include a metered quantity of an antigenic peptide in accordance with the invention, together with a means for detecting immunocomplexes between the antigen and its antibody component. The term "metered" in the context of the invention refers to aliquots of antigen having a predetermined or quantified antigenic reactivity such that a measured amount of the Ro/SS-A antigenic material will provide roughly expected level of immunoreactivity, such as, e.g., in terms of chromogenic reactivity in an ELISA assay.

Useful immunocomplex detecting means are generally well known in the art, and include materials such as an antibody having specificity for the Ro antigenic substance, or an anti-Ig having specificity for antibodies of, e.g., human origin. In either case, the detecting means would include a label such as a radioactive ligand or a chromogenic enzyme such as horseradish peroxidase, alkaline phosphatase, or urease, on even using the avidin-biotin reaction. In certain embodiments, for example, in an RIA-directed kit, it is contemplated that the detecting means may include a label, whether radio-active, enzymatic or the like, attached directly to the Ro antigenic material itself. In such embodiments, the detecting means functions by allowing one to detect or even quantify the interaction between an antibody and the labeled antigen, or the ability of the labeled antigen to compete for immunoadsorption with the antibody. In any case, the design of kits of the foregoing nature will be apparent to those of skill in the art in light of the present disclosure and previous teachings such as U.S. Pat. Nos. 4,454,233; 4,446,232 or 4,376,110; all incorporated herein by reference.

BRIEF DESCRIPTION OF THE DRAWINGS

FIGS. 2A and 2B. The 1.9 kb Ro cDNA nucleic acid and encoded amino acid sequence. The 1890 base coding strand encodes a 417 amino acid polypeptide which includes four previously determined amino acid sequences (underlined) from sequencing the native protein and cyanogen bromide and *Staph. aureus* V8 cleavage products. The eukaryotic ribosomal consensus sequence for the initiation of translation is boxed and the putative polyadenylation signal is overlined.

Figure 3A:
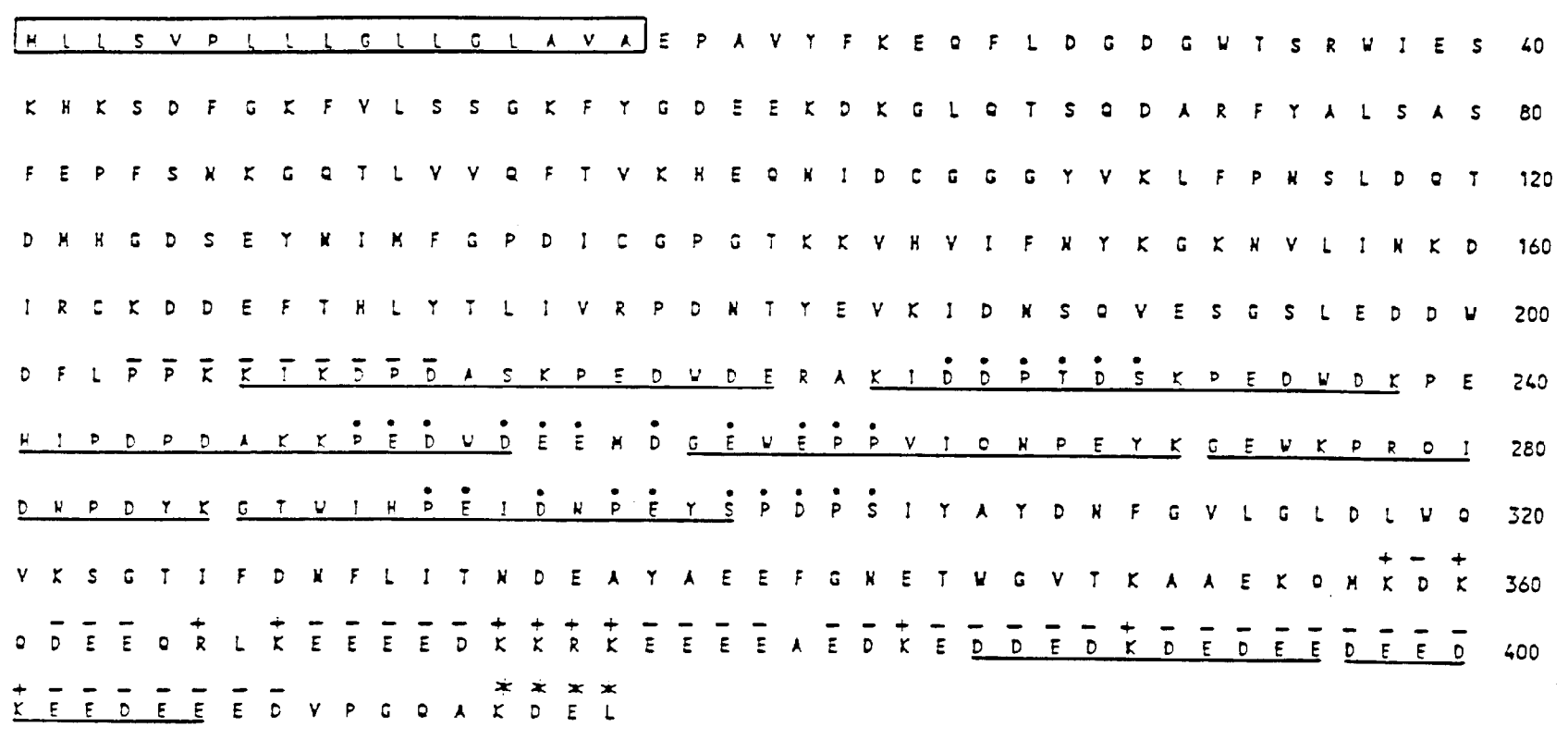

FIG. 3. A. The Ro cDNA encoded amino acid sequence. The hydrophobic leader segment is boxed, the sequences corresponding to two synthetic peptides with antigenic activity are in parentheses and a putative nuclear targeting signal is overlined with a broken line. The two sets of internal sequence duplications are underlined and three of the PEST, D rich areas are indicted by overlying dots. The negatively charged amino acids at the carboxy terminal end are indicated by (–) signs and the KDEL carboxy-terminal endoplasmic reticulum retention signal sequence is overlined with stars. B. The two sets of internal duplications are aligned for ease of comparison. The numbers represent the amino acid sequence position.

DETAILED DESCRIPTION OF THE PREFERRED EMBODIMENTS

Introduction

Figure 1:
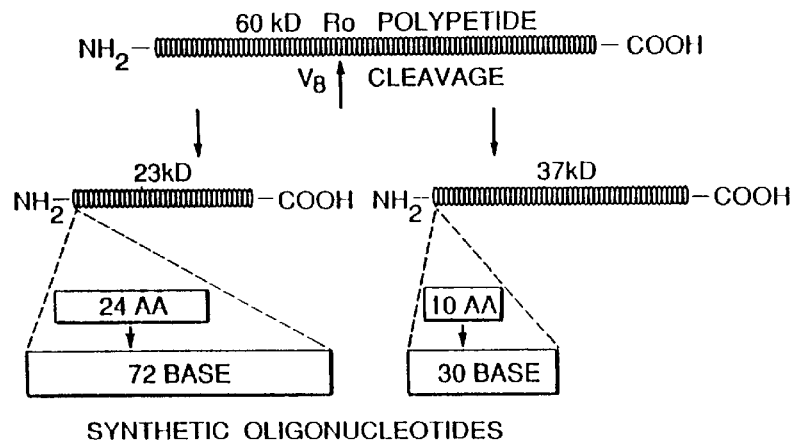
FIG. 1. Synthetic oligonucleotide construction. The native 60 kD Ro polypeptide was purified from a Wil-2 cell extract and subjected to a limited *Staph. aureus* V8 protease digestion which cleaved the 60 kD polypeptide into a 23 and 37 kD domain. The amino terminus of each domain was sequenced and this amino acid sequence information was converted into the most probable nucleic acid sequence for the construction of two non-degenerate synthetic oligonucleotides.

Prior to the present invention, the immunoanalysis of autoimmune disease antibodies of the anti-Ro/SS-A type has required the use of the Ro/SS-A antigen itself, a complex antigen which includes both RNA and protein substituents bound together in a particular ribonucleoprotein ("RNP") particle. Unfortunately, use of the Ro/SS-A RNP particle in the characterization of this disease is fraught with difficulties which range from the relative scarcity of the Ro/SS-A RNP particle and low yields associated with its isolation from natural sources, to difficulties associated with the stability of the Ro RNP particle upon storage under economically and/or commercially reasonable storage conditions. While the former problems arise in part from the low level production of the Ro particle in sources such as human or bovine spleen tissue or human B-cell lines, the latter problems are likely attributable to the prevalent nature of ribonucleases and proteases or perhaps the complex structure of the particle.

The present invention is directed to solving these and other problems through the surprising discovery by the inventors that a relatively short peptide sequence can substitute for the much larger, RNA/protein particle complex in immunocharacterization studies and assays. In that such sequences can be readily synthesized by a variety of means, including chemically synthetic or even recombinant techniques, the peptides are relatively easy to prepare in economical quantities. Moreover, in that the antigen so produced is a simple peptide structure rather than an RNP particle or a large naturally occurring protein such as the 60 Kd protein antigen, storage and use by a variety of manners is thereby enabled.

The present invention is further directed to nucleic acid which encodes the 60 kD Ro antigen, and/or which corresponds to a portion of the antigen gene. This aspect of the invention arises out of the inventors preparation, isolation and subsequent sequencing and analysis of cDNA sequences corresponding to the 60 kD Ro antigen mRNA. This information, disclosed herein in FIG. 2, allows the preparation of the 60 kD antigen by recombinant means as well as enabling the preparation, by means of DNA engineering techniques such as site-directed mutagenesis, of so-called second generation peptides which incorporate desired sequence attributes of the 60 kD sequence, such as the incorporation of antigenic core sequences, or which incorporate selected mutations or variations into 60 kD antigen sequences, e.g., in order to achieve a desired improvement, such as an improvement in antigenic function.

In addition to their usefulness in the preparation of peptides, the nucleic acid sequences disclosed herein may be employed to take advantage of their ability to hybridize to corresponding 60 kD Ro antigen gene sequences. Thus, the sequence information of FIG. 2 will find utility in a variety of embodiments which take advantage of this property, e.g., in the screening of clone banks, both first and second generation banks, in probing the structure of the 60 kD Ro antigen genomic gene, in testing for the presence of 60 kD antigen gene sequences in biological samples, such as skin or heart tissue.

Polypeptides of the Invention

Polypeptides of the invention are defined in their most basic sense as including one or more of the following amino acid stretches, which have been identified as a Ro/SS-A epitopic core sequence:

-phe-lys-glu-gln-phe-leu-asp-gly-asp-gly-trp-thr-asp/ser-arg-;

-lys-glu-gln-phe-leu-asp-gly-asp-gly-trp-thr-asp/ser-arg-trp-ile-glu-ser-;

-asn-ser-gln-val-glu-ser-gly-ser-leu-glu-asp-asp-trp-asp-phe-leu-pro-pro-lys-lys-ile-lys-;

-his-ile-pro-asp-pro-asp-ala-lys-lys-pro-glu-asp-trp-asp-glu-;

Syntheses of the foregoing epitopic core sequences, or peptides which include the foregoing within their sequence, is readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of the peptides of the invention, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris to maintain a pH of 7.0 to 7.5. Moreover, it may be desirable to include agents which will inhibit microbial growth, such as sodium azide. For extended storage in an aqueous state it will be desirable to store the solutions at 4° C., or more preferably, frozen.

Of course, where the peptide(s) are stored in a lyophilized or powdered state, they may be stored virtually indefinitely, e.g., in metered aliquots that may be rehydrated with a predetermined amount of water (preferably distilled) prior to use.

Biological Functional Equivalent Amino Acids

As discussed above, it is generally known in the art that certain amino acids may be substituted for other amino acids in a protein structure without appreciable loss of interactive binding capacity with complementary structures such as antigen-binding regions of antibodies (or, e.g., binding sites on receptor molecules). It is thus hypothesized by the present inventors that various changes may be made in the sequence of the antigenic peptides without appreciable loss of their antibody-binding, or Ro/SS-A antigen competing, activity.

The importance of the hydropathic index of amino acids in conferring interactive biologic function on a protein has been discussed generally by Kyte et al. (16), wherein it is found that certain amino acids may be substituted for other amino acids having a similar hydropathic index or score and still retain a similar biological activity. As displayed in the table below, amino acids are assigned a hydropathic index on the basis of their hydrophobicity and charge characteristics. It is believed that the relative hydropathic character of the amino acid determines the secondary structure of the resultant protein, which in turn defines the interaction of the protein with substrate molecules.

TABLE I

| Amino Acid | Hydropathic Index |
| --- | --- |
| Isoleucine | 4.5 |
| Valine | 4.2 |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |

TABLE I-continued

| Amino Acid | Hydropathic Index |
| --- | --- |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

Thus, for example, isoleucine, which has a hydropathic index of +4.5, can be substituted for valine (+4.2) or leucine (+3.8), and still obtain a protein having similar biologic activity. Alternatively, at the other end of the scale, lysine (−3.9) can be substituted for arginine (−4.5), and so on.

Accordingly, these amino acid substitutions are generally based on the relative similarity of R-group substituents, for example, in terms of size, electrophilic character, charge, and the like. Substitutions which take various of the foregoing characteristics into consideration include the following:

TABLE II

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala |
| His | asn; gln |
| Ile | leu; val |
| Leu | ile; val |
| Lys | arg; gln; glu |
| Met | met; leu; tyr |
| Ser | thr |
| Thr | ser |
| Trp | tyr |
| Tyr | trp; phe |
| Val | ile; leu |

Immunoassays

It is proposed that the peptides of the invention will find their greatest utility in immunoassays for the detection of Ro/SS-A reactive antibodies. In their most simple and direct sense, preferred immunoassays of the invention include enzyme linked immunosorbent assays (ELISAs), but, as discussed above, utility is clearly not limited to such assays.

In the preferred ELISA assay, peptides incorporating the Ro/SS-A epitopic core sequences are immobilized onto a selected surface, preferably a surface exhibiting a protein affinity such as the wells of a polystyrene microtiter plate. After washing to remove incompletely adsorbed material, one will desire to bind or coat a nonspecific protein such as bovine serum albumin (BSA) or casein onto the well that is known to be antigenically neutral with regard to the test antisera. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera to be tested in a manner conducive to immuno-complex formation. Such conditions preferably include diluting the antisera with diluents such as BSA, bovine gamma globulin (BGG) and phosphate buffered saline (PBS)/Tween. These added agents also tend to assist in the reduction of nonspecific background. The layered antisera is then allowed to incubate for from 2 to 4 hours, at temperatures preferably on the order of 25° to 27° C. Following incubation, the antisera-contacted surface is washed so as to remove non-immunocomplexed material. A preferred washing procedure includes washing with a solution such as PBS/Tween, or borate buffer.

Following formation of specific immunocomplexes between the test antisera and the bound antigen, and subsequent washing, the amount of immunocomplex formation may be determined by subjecting to a second antibody having specificity for the first. Of course, in that the test antisera will typically be human antisera, the second antibody will preferably be an antibody having specificity in general for human Ig. To provide a detecting means, the second antibody will preferably have an associated enzyme that will generate a color development upon incubating with an appropriate chromogenic substrate. Thus, for example, one will desire to contact and incubate the antisera-bound surface with a peroxidase-conjugated anti-human IgG for a period of time and under conditions which favor the development of immunocomplex formation (e.g., incubation for 2 hours at room temperature in a PBS-containing solution such as PBS-Tween).

After incubation with the second, enzyme-tagged antibody, and subsequent washing to remove unbound material, the amount of label is quantified by incubation with a chromogenic substrate such as 2,2-azino-di-(3-ethyl-benzthiazoline-6-sulfonic acid ([ABTS] and $H_2O_2$, in the case of peroxidase as the enzyme label. Quantification is then achieved by measuring the degree of color generation, e.g., using a visible spectra spectro-photometer.

Nucleic Acid Sequences of the Invention

Figure 2A:
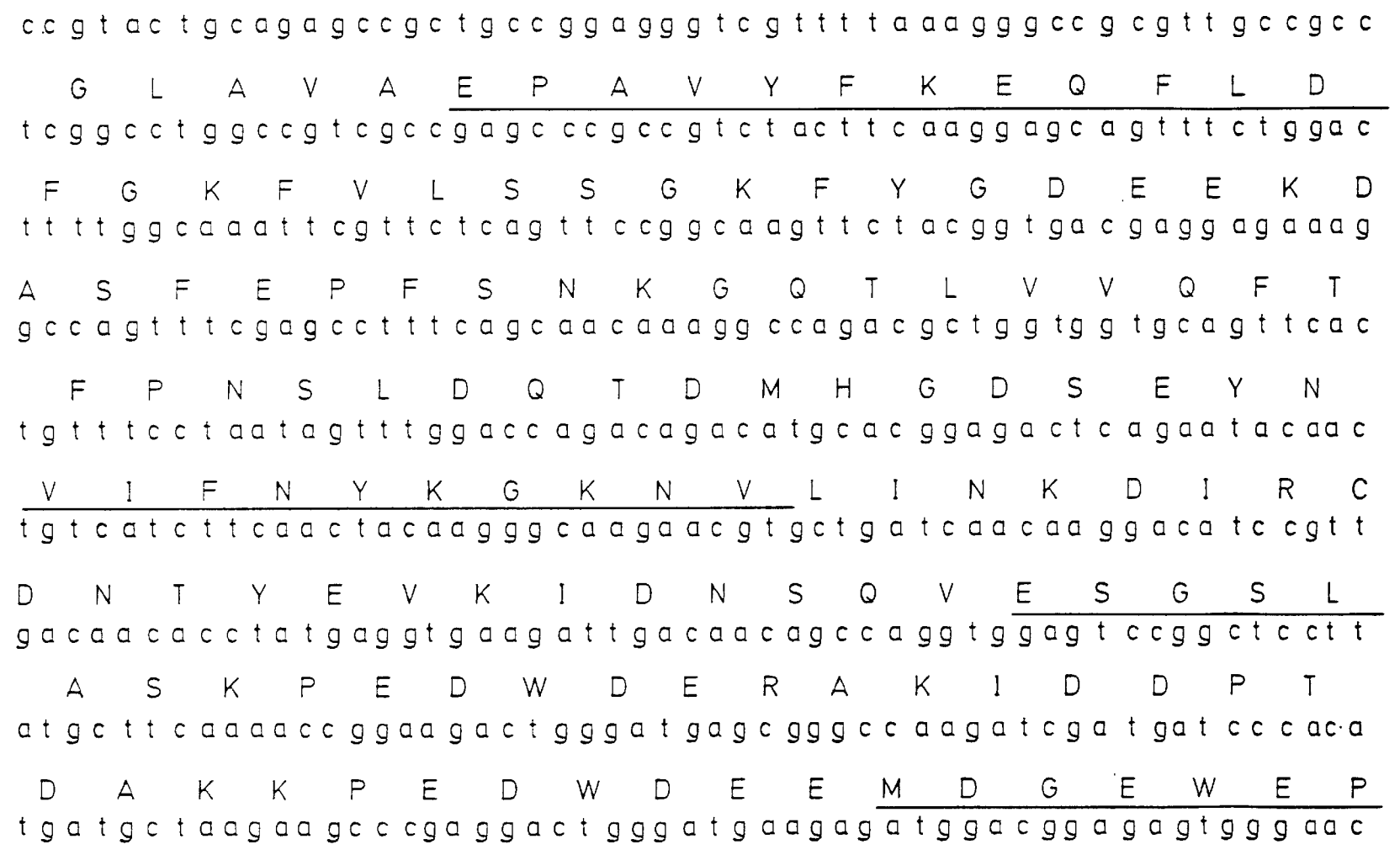
Figure 2B:
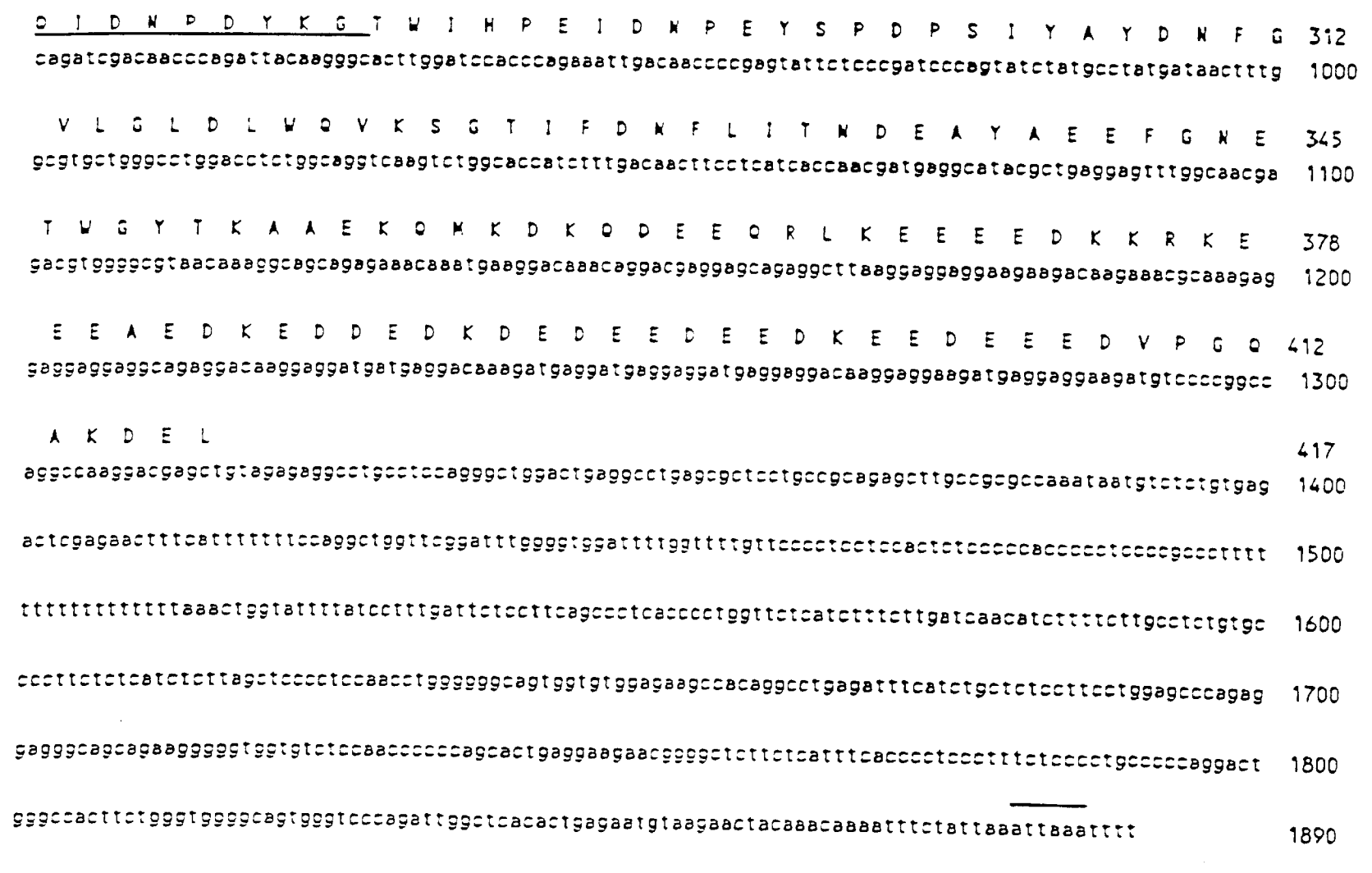
Figure 2B:
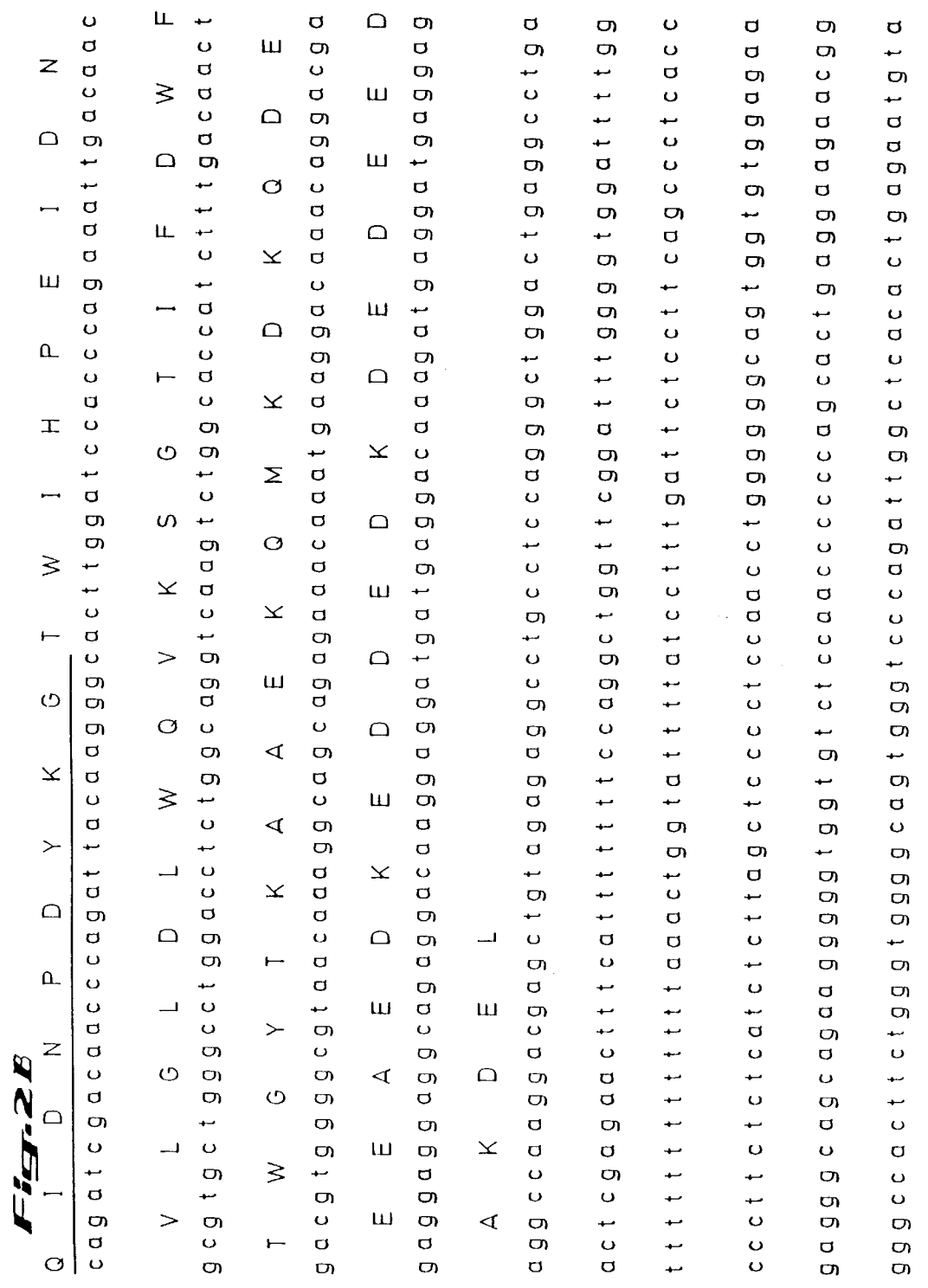

Nucleic acid sequences of the invention are defined in their most basic sense as either 1) nucleic acid sequences which encode a sequence of amino acids which includes within its sequence at least an epitopic core sequence of the amino acid sequence of FIG. 2, or 2) nucleic acid sequences which are capable of forming a stable hybrid duplex with the 60 kD Ro antigen gene sequences. Thus, included within category 1) are nucleic acid sequences which encode peptides or proteins which incorporate any of the antigenic peptide sequences discussbd above. of course, due to codon redundancy or perhaps the desire to incorporate variations, the actual DNA or RNA sequence constructed and/or otherwise obtained and employed may vary from that actually found in nature, and thus may vary from that set forth in FIG. 2.

The category 2) nucleic acid sequences will generally find their greatest use as hybridization probes, e.g., to detect the presence of corresponding sequences in a biological sample. For such applications, it will generally be necessary to prepare probes having a stretch of nucleotides long enough to form a stable hybrid duplex with the projected target sequence. For this reason, category 2) nucleic acids will generally include at least a 14 nucleotide long region that is complementary to, or which corresponds to, the 60 kD Ro antigen sequence as set forth in FIG. 2. The reason that such nucleic acid molecules can either be "complementary to" or "corresponding to" the FIG. 2 sequence is that the ultimate target nucleic acid, if DNA, will include both complementary DNA strands, with each complementary strand being available for probing.

To prepare nucleic acid sequences for use in accordance with the invention, one may desire to employ either recombinant or synthetic means. Where only short stretches of DNA are needed, e.g., having a length on the order of 30 to 40 or so nucleotides, one may desire to prepare the desired segment(s) synthetically, such as through the use of readily available DNA synthesizing technology. Due to a practical limitation on the size of nucleotides that can readily be prepared synthetically, such chemical synthetic preparation techniques will likely find their greatest utility in the preparation of segments for use as hybridization probes. However, a synthetic approach should not be ruled out when one seeks to prepare translational units for use, e.g., in the recombinant production of antigenic peptides, particularly where the preparation of only smaller peptides is contemplated.

For certain applications, e.g., where larger nucleic acid polymers are required, one will generally find it most advantageous to prepare suitable nucleic acid polymers by recombinant techniques. The most preferred approach is cDNA cloning in that a nucleic acid molecule is obtained having a transcription unit that does not require RNA splicing of the subsequent RNA transcript. This, of course, allows one to employ prokaryotic hosts for recombinant production of antigenic peptides. As is appreciated in the art, such hosts can not readily be employed to produce recombinant peptides where intron-containing coding sequences such as genomic sequences are used, due to the inability of the host to faithfully process the RNA intermediate.

In preferred embodiments, the most desired source of DNA segments encoding the 60 kD Ro antigen gene will be directly from the inventors' deposit of biological material with the ATCC (plasmid pGEM containing Ro cDNA recombinant insert; deposited with ATCC on Mar. 21, 1989 and accorded accession number 40583). From this deposit, which includes DNA containing the entire coding sequence of the 60 kD Ro antigen gene, as well as both 3' and 5' untranslated regions, one can readily prepare subfragments, desired restriction fragments, and even as a starting point for the preparation of second generation materials, e.g., as a template for site-directed mutagenesis. However, where one desires to clone the 60 kD Ro antigen gene de novo, the sequence information provided by FIG. 2 can be employed to prepare appropriate probes.

In general, cDNA cloning of the 60 kD Ro antigen gene can be performed through the preparation and screening of a CDNA clone bank such as disclosed below in the examples. Due to the finding that they contain ample amounts of 60 kD Ro antigen RNA sequences, a preferred source of starting poly A+RNA for use in cDNA construction is the Wil-2 B-cell line. This line is an Epstein-Barr virus transformed B-cell line that is readily available from a variety of sources, such as the Mutant Cell Repository. However, it is believed that other sources of starting mRNA can be successfully employed, including, e.g., any B cell line, such as can be obtained from public cell repositories like the ATCC. In the Wil-2 line, the 60 kD Ro antigen mRNA sequences are somewhat rare, on the order of about 1:10,000 molecules. Therefore, one will generally desire to prepare a bank having at least about $1 \times 10^6$ members to ensure the presence of a full length cDNA transcript.

Screening of the bank is preferably preformed by oligo probing, and preferably using a nucleotide hybridization probe selected from a region towards the amino terminus of the gene, as shown in FIG. 2. It may be further desirable to employ an additional probe which corresponds to a different portion of the gene, such as a more internal or even carboxy-terminal region. Conditions found to work well in the hybridization screening are disclosed hereinbelow. Preferred hybridization conditions for probe hybridizations in general will be fairly stringent conditions of 6×SSC, at 42 degrees for 18 hours, followed by washing with 1×SSC for 2 hours at 42° C.

Once the full length gene, or a desired subportion thereof, has been obtained by whatever means, recombinant production of Ro 60 kD antigen sequences is obtained by emplacing the transcriptional unit upstream of, and under the control of, a suitable promoter and transforming a suitable host with the constructed recombinant gene. Often, the recombinant transcription unit will be packaged into a recombinant vector, such as a plasmid, phage or virus, which contains an origin of replication and usually a selection marker sequence such as an antibiotic resistance marker. The inventors contemplate that either prokaryotic or eukaryotic systems can be employed, as discussed in more detail below. Following transformation of an appropriate host with the recombinant transcriptional construct, the transformed host is grown under conditions selected to promote transcription and subsequent translation of the recombinant sequences. As understood by those of skill in the art the conditions ultimately selected will generally depend on the nature of the transcriptional construct and the promoter that is employed.

A preferred construct for recombinant expression of 60 kD Ro antigen sequences, whether it be the full length gene or subportions or variants thereof, includes the use of the bacteriophage T7 RNA polymerase/promoter system, as described by Tabor et al., or the use of the baculovirus expression system (polyhedron promoter) as described by Summers. The use of both of these systems is well understood by those of skill in the art of recombinant expression, as exemplified by references 74 through 76.

After expression of the recombinant 60 kD antigen sequence, the recombinant protein can be collected by lysis of the bacteria, and purification is by fractionation and column chromatographic techniques, e.g., as detailed for the isolation of native Ro/SS-A in Example I below.

Site-Specific Mutagenesis

As noted above, site-specific mutagenesis is a technique useful in the preparation of individual peptides, or biologically functional equivalent proteins or peptides, derived from the 60 kD antigen sequence, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications such as reference 28, incorporated herein by reference. As will be appreciated, the technique typically employs a phage vector which exists in both a single stranded and double stranded form. Typical vectors useful in site directed mutagenesis include vectors such as the M13 phage, for example, as disclosed by reference 29, incorporated hereby in reference. These phage are readily commercially available and their use is generally well known to those skilled in the art.

In general, site-directed mutagenesis in accordance herewith is performed by first obtaining a single-stranded vector which includes within its sequence a DNA sequence which encodes all or part of the 60 kD Ro antigen. An oligonucleotide primer bearing the desired mutated sequence is prepared, generally synthetically, for example by the method of reference 30. This primer is then annealed with the singled-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells and clones are selected which include recombinant vectors bearing the mutated sequence arrangement.

Host Cell Cultures and Vectors

In general, of course, prokaryotes are preferred for the initial cloning of DNA sequences and constructing the vectors useful in the invention. For example, E. coli. DH5 or K12 strain 294 (ATCC No. 31446) are particularly useful: Other microbial strains which may be used include E. coli strains such as E. coli B, and E. coli X 1776 (ATCC No. 31537). These examples are, of course, intended to be illustrative rather than limiting.

Prokaryotes may also be used for expression. The aforementioned strains, as well as E. coli W3110 (F-, lambda-, prototrophic, ATCC No. 273325), bacilli such as Bacillus subtilus, or other enterobacteriacea such as Salmonella typhimurium or Serratia marcesans, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR 322, a plasmid derived from an E. coli species (see, e.g., ref. 31). pBR 322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

Those promoters most commonly used in recombinant DNA construction include the B-lactamase (penicillinase) and lactose promoter systems (32–34) and a tryptophan (trp) promoter system (35,36). While these are the most commonly used, other microbial promoters have been discovered and utilized, and details concerning their nucleotide sequences have been published, enabling a skilled worker to ligate them functionally with plasmid vectors (36).

In addition to prokaryotes, eukaryotic microbes, such as yeast cultures may also be used. Saccharomyces cerevisiase, or common baker's yeast is the most commonly used among eukaryotic microorganisms, although a number of other strains are commonly available. For expression in Saccharomyces, the plasmid YRp7, for example, is commonly used (37–39). This plasmid already contains the trpl gene which provides a selection marker for a mutant strain of yeast lacking the ability to grow in tryptophan, for example ATCC No. 44076 or PEP4-1 (40). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (41) or other glycolytic enzymes (42–43), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebtate culture. However, interest has been greatest in vertebrate cells, and propagation of vertebrate cells in culture (tissue culture) has become a routine procedure in recent years (44). Examples of such useful host cell lines are VERO and HeLa cells, Chinese hamster ovary (CHO) cell lines, and W138, BHK, COS-7 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (45). Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

As origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

EXAMPLE I

The present example was undertaken to illustrate a preferred embodiment of the invention. The example thus employs laboratory techniques found by the inventors to work well in the context of the present invention. However, it will be apparent to those of skill in the art that various alterations and modifications, including changes in reagents and amounts of materials, may be made in these particular techniques in light of the present disclosure without departing from the spirit and scope of the invention.

Peptide Synthesis

A peptide, designated epitopic core sequence I (ECS-I), consisting of the following sequence of amino acids was synthesized with a cysteine residue added at its amino terminus, using an Applied Biosystems Model 430A Peptide Synthesizer:

-phe-lys-glu-gln-phe-leu-asp-gly-asp-gly-trp-thr-asp-arg-. The peptide was then deprotected by HF cleavage. The peptide was then sequenced as disclosed below to confirm the sequence. A portion of the synthesized peptide material w&s conjugated to keyhole limpet haemocyanin (KLH).

The following peptide, designated ECS-II, was also prepared in the above manner:

-lys-glu-gln-phe-leu-asp-gly-asp-gly-trp-thr-asp-arg-trp-ile-glu-ser-.

Protein Sequencing

The above antigen peptide preparations were subjected to peptide sequencing by automated Edman degradation using either a gas phase Model 470 Applied Biosystems Sequencer (Foster City, Calif.) with the Model 120, on-line HPLC PTH amino acid identification system, or a Beckman spinning cup Model 890M sequencer (Palo Alto, Calif.). In the later case, the PTH amino acids were identified using a Nova Pac column in a Waters Model 840 HPLC system (Millford, Mass.).

Purification of Native Ro/SS-A Antigen

Antigen source. The Ro/SS-A antigen was isolated from an extract of an Epstein-Barr virus transformed human B-lymphoblastoid cell line (Wil-2). The cells were grown in Eagle's medium supplemented with 2 mM glutamine, sodium pyruvate, non-essential amino acids, 10% fetal calf serum, penicillin (10,000 U/ml) and streptomycin (10 mg/ml). The cells were centrifuged at 35 xg for 12 minutes and washed with phosphate-buffered saline (0.14M NaCl, 0.01M phosphate, pH 7.4) (PBS) 3 times. The packed cells were mixed with the same volume of PBS containing 1 mM phenyl-methyl sulfonyl fluoride (PMSF). The suspension was sonicated on ice with ten 15-second pulses using a Heat System Sonicator at a setting of 9. The sonicate was then centrifuged at 12,100 xg for 1 hour and the supernatant subjected to ammonium sulfate precipitation as described by Lieu et al. (17).

The ammonium sulfate fractions were pooled and dialyzed against 24 mM borate buffer, pH 7.6, and applied to a polybuffer ion exchange column. After washing the column with 24 mM borate buffer (eluate with OD280>0.1), a stepwise sodium chloride gradient was applied to the column. The majority of La/SS-B antigen was eluted in the 0.1M and 0.2M sodium chloride fraction whereas all the Ro/SS-A antigen was recovered in the 0.5M and 1M sodium chloride fractions. After concentration by ammonium sulfate precipitation, a modest amount of La/SS-B activity was also detected in the 1M NaCl fraction by counterimmunoelectrophoresis against prototypic antisera.

The antigenically active material from the PBE column (0.5M and 1M NaCl fraction) was further purified by electrophoresis in a 5.6% native polyacrylamide gel (N-PAGE). After electrophoresis, the gel was divided into a series of 10 mm slices and the material was eluted from the gel with distilled water. By counterimmunoelectrophoresis (CIE), maximal Ro/SS-A antigen activity was located in the fraction with an Rf of 9.0 whereas the maximal La/SS-B activity was recovered in the region with an Rf of 0.7. When the antigenically active fraction from the N-PAGE was subjected to SDS-PAGE it contained a single stained band of 60,000 molecular weight whose identity was confirmed by Western blot analysis.

Human antisera. Anti-Ro/SS-A sera were selected by the presence of a single precipitin line in Ouchterlony analysis having complete identify with prototypic sera used in studies of Lieu et al. (17). The absence of antibodies to other nuclear antigens such as La/SS-B, U1 -RNP and Sm was also confirmed by ELISA. Monospecific anti-Sm and anti-La/SS-B human autoimmune sera were originally obtained from the laboratory of Dr. E. M. Tan (Scripps Research Institute, La Jolla, Calif.). Each formed a single precipitin line in double immunodiffusion analysis with the appropriate antigens and did not react with purified Ro/SS-A in the ELISA.

Immunization Protocol

Female rabbits (New Zealand, White) were immunized subcutaneously in the neck region with 0.5 mg of peptide conjugated to KLH emulsified in Freund's complete adjuvant (FCA). At one week, the animals were similarly immunized with 1 ug of the unconjugated peptide alone. At monthly intervals thereafter the rabbits were boosted with the KLH-conjugated peptide emulsified in FCA.

Enzyme-linked Immunosorbent Assay (ELISA)

The native Ro/SS-A antigen (5 ug/ml) or synthetic peptide (10 ug/ml) in PBS was added to wells of a microtiter plate and incubated 16 hours at 4° C. The plates were washed with PBS-Tween and the remaining sites were coated with 1% BSA for 1 hour. After washing 3 times with PBS-Tween, sera diluted with 1% BSA, 0.5% bovine gamma globulin (BGG) in PBS-Tween were added and incubated for 2 hours. The plates were then washed 3 times with PBS-Tween. Peroxidase conjugated goat-anti-human IgG diluted 1:3000 in PBS-Tween containing 1% BSA and 0.5% BGG was added and incubated for 2 hours at room temperature. The plates were washed in a similar manner. The color was developed by adding a peroxidase substrate solution containing 1 mg/ml of 2,3'-azino-di-(3-ethyl-benzthiazoline-6-sulfonic acid) (ABTS) and 0.005% $H_2O_2$ in 0.1M McIvaine's buffer, pH 4.6. The optical density was measured using a Titertek Multiskan brand ELISA plate reader.

To determine the proportion of the total native Ro/SS-A antigenic activity that is present on the synthetic peptides, increasing amounts of KLH-coupled synthetic peptide were preincubated with a monospecific patient anti-Ro/SS-A serum. After a 16 hours incubation at 4° C., the inhibited serum aliquots were diluted to the appropriate concentrations and added to a native Ro/SS-A antigen-coated plate. The degree of inhibition was then calculated by comparison with the reactivity of untreated anti-Ro/SS-A serum.

Results

Human autoimmune serum to Ro/SS-A was diluted 1:100 and reacted with both the synthetic peptide ECS-I and ECS-I conjugated to KLH (Table III). Whereas the binding to anti-Ro/SS-A serum was quite strong, reaction of the synthetic peptides with human autoimmune sera specific for other antigens such as Sm, La/SS-B and normal human sera did not produce significant binding. Furthermore, the binding of anti-Ro/SS-A sera to the ECS-I peptide was completely blocked by preincubating the sera with native Ro/SS-A antigen. Finally, anti-Ro/SS-A sera which show strong binding to the ECS-I did not react in ELISA with control polypeptides such as ribonuclease A or an unrelated synthetic peptide conjugated to KLH.

TABLE III

REACTIVITY OF ECS-I WITH HUMAN AUTOIMMUNE SERA

| Immobilized Antigen | Antibody | ELISA OD405 |
| --- | --- | --- |
| KLH-Synthetic peptide ECS-I | Anti-Ro/SS-A | 1.823 |
| | Anti-Sm | 0.288 |
| | Anti-La/SS-B | 0.355 |
| | Normal serum | 0.263 |
| Synthetic peptide ECS-I | Anti-Ro/SS-A | 1.059 |
| | Anti-Sm | 0.236 |
| | Anti-La/SS-B | 0.158 |
| | Normal serum | 0.118 |

Moreover, the ECS peptides demonstrated a strong ability to compete with the native Ro/SS-A RNP particle for binding to anti-Ro antisera. Exemplary studies showing the inhibition of binding of a monospecific human anti-Ro/SS-A serum to native Ro/SS-A antigen in ELISA by synthetic peptide ECS-II is shown in Table IV.

TABLE IV

INHIBITION OF THE BINDING OF A MONOSPECIFIC HUMAN ANTI-Ro/SS-A SERUM TO NATIVE Ro/SS-A ANTIGEN BY KLH-ECS-II

| KLH-ECS-II (ug) | Percent Inhibition |
| --- | --- |
| 2 | 11.9 |
| 6 | 17.0 |
| 8 | 27.3 |
| 12 | 28.4 |
| 16 | 39.2 |
| 24 | 29.0 |
| 30 | 32.0 |

In order to further characterize the Ro/SS-A antigen, an antiserum to ECS-I was raised by immunizing a rabbit with KLH-ECS-I. The antibody level in rabbit serum (diluted 1:100) was measured by ELISA against native human Ro/SS-A antigen as well as the synthetic peptide. Elevated binding to Ro/SS-A antigen ($OD_{405}$=0.1565 for pre-immune rabbit sera) was detected. The binding of rabbit anti-peptide ECS-I to native human Ro/SS-A antigen was quantitatively inhibited by KLH ECS-I (Table V). The results of these experiments indicate that the epitope represented by the ECS-I sequences corresponded to an epitope on the outer surface of native Ro/SS-A. It is possible, however, that distortion might occur when coating the native Ro/SS-A protein to the ELISA plate, allowing the ECS-I epitope to become relatively more exposed. This is also consistent with the finding that some prototypic human autoimmune sera to Ro/SS-A antigen reacted with the synthetic peptide.

TABLE V

INHIBITION OF THE BINDING OF RABBIT ANTI-ECS-I ANTISERUM TO NATIVE HUMAN Ro/SS-A ANTIGEN

| KLH-ECS-I (ug) | Percent Inhibition |
| --- | --- |
| 8 | 79 |
| 10 | 88 |
| 16 | 98 |

From the foregoing examples, it will be apparent to those of skill in the art that the two epitopic core sequences, ECS-I and ECS-II, comprise useful functional antigenic equivalents of the native Ro/SS-A RNP particle antigen. For example, serum from rabbits immunized with KLH-ECS-I showed antibody activity toward native human Ro/SS-A antigen, confirming that the ECS-I peptide possessed the combination of properties which are essential for antibody binding. The sites most frequently recognized by antibodies form three-dimensional super-assemblies characterized by high local mobility, convex surface shapes, and negative electrostatic potential (18). The sequence data indicates that the ECS peptides carry a negative charge. Delineation of the exact location of sub-epitope(s) within the ECS sequences which binds to human autoantibody and to antibodies raised in rabbits will be of interest. In this way, the influence of the microenvironment on antigenic sites within peptides can be approached. In addition, the antiserum to KLH-ECS will be useful in determining the tissue distribution as well as cellular localization of native human Ro/SS-A antigen. Also, antiserum to the ECS peptides could be used as a probe for identifying epitopic fragment(s) of the native Ro/SS-A molecule following proteolytic cleavage. Such studies could provide further insight regarding the structure of the native molecule.

Relatively few amino acid sequences of "autoantigens" that react with autoimmune sera from patients with rheumatic disease have yet been elucidated. The carboxyl terminal 55 amino acids of the La/SS-B antigen was recently identified by analyzing overlapping cDNA clones (19). There is no apparent sequence homology between the ECSs of the present invention and these sequences of La/SS-B.

Synthetic peptides have been widely applied as probes for the study of DNA-binding sites on protein (21), T and B-cell recognition sites on protein antigens (18, 21–24), and peptide binding sites on Ia molecules (25). The results of recent studies using synthetic peptides in combination with crystallographic studies indicate that initial binding to solvent exposed amino acid residues may promote local side-chain displacements and thereby allow the participation of other, previously buried residues (26). The fact that synthetic ECS-I reacted with monospecific specific antibodies to Ro/SS-A in human autoimmune sera indicates a primary contact amino acid residue(s) is located on this peptide. Indeed, data indicate that the tripeptide, -asp-gly-trp-, is likely involved in initial antibody recognition.

It is proposed that the use of synthetic peptides in accordance with the invention will likely provide a superior method than is currently available for detecting anti-Ro/SS-A antibodies in the sera of patients with autoimmune disease. The advantages provided by the synthetic peptide include the availability of a quality controlled antigen in large amounts, the ability to automate the procedure and the lower background and higher sensitivity of a synthetic peptide-based ELISA technique. Present anti-Ro/SS-A assays are complicated by the recent observation which suggests that some epitopes on the Ro/SS-A antigen are cross-reactive with IgG (27). The use of synthetic peptides to mimic Ro/SS-A epitopes could provide advantages since the two different types of epitopes (Ro/SS-A only vs. Ro/SS-A plus IgG) could be separately analyzed. In fact, recent preliminary results from the inventors laboratory suggest that sera from patients with different clinical disorders such as SCLE and Sjogren's syndrome and children with congenital heart block show different frequencies of reactivity to the ECS-I epitope. The idea that variability might exist in the autoimmune response to different epitopes on the same molecule is supported by recent studies which have indicated that rabbits actively immunized against myohemerythrin also demonstrate a variable antibody response to different epitopes on this polypeptide (19).

EXAMPLE II

In this example is described the screening of a human hybridoma cell complementary DNA (cDNA) library and the isolation of a cDNA clone which encodes a 60 kD Ro autoantigen. As shown in FIG. 2, the 1890 base pair recombinant insert contained an open reading frame that encoded a 417 amino acid polypeptide which included the 18 amino acid sequence Ro epitopic core sequence addressed above in Example I. The coding region begins with an AUG codon as part of a sequence which bears homology to the eukaryotic ribosomal consensus sequence for the initiation of translation. The initial methionine was followed by a strongly hydrophobic 16 amino acid leader segment. There was a 66 base pair 5' untranslated segment and a 573 base pair 3' untranslated segment which begins with a UAG termination codo and included a single putative polyadenylation signal. The nucleic acid sequence and its encoded amino acid sequence did not bear strong homology to other published sequences. Southern filter hybridization analysis indicated that this gene was not highly polymorphic and existed as a single copy in the human genome. Chromosomal localization studies place this gene on the short arm of chromosome 19 near the LDL receptor gene.

MATERIALS and METHODS

The enzymes used in the various recombinant nucleic acid techniques were obtained from Promega Biotec, Madison Wis. or Pharmacia, Inc., Piscataway, N.J., unless stated otherwise.

Protein Purification and Sequence Analysis

The Ro protein antigen was purified from the human Wil-2 cell line (an Ebstein-Barr virus transformed lymphoblastoid B-cell line) as described (46). *Staphlococcus aureus* V8 (Berhinger Mannheim Biochemicals, Indianapolis, Ind.) and cyanogen bromide (Sigma Chemicals Co., St. Louis, Mo.) cleavage fragments were generated (47) and sequenced on an Applied Biosystems 470A protein sequencer/120A PTH Analyzer (Applied Biosystems, Foster City, Calif.), as previously described (46).

Deglycosylation Analysis

The purified Ro protein was digested with Neuraminidase, Endo-a-N-Acetylgalactosaminidase and Glycopeptidase F according to the manufacturer's recommendations (Boehringer Mannheim Biochemicals), and then subjected to sodium dodecyl sulfate-polyacrylamide gel electrophoresis (SDS-PAGE).

Synthetic Oligonucleotide Construction

A codon utilization table was employed to convert the amino acid sequence data into its most probably nucleic acid sequence (48). The oligonucleotides were synthesized on an Applied Biosystems 380B DNA synthesizer.

cDNA Library Construction

Total RNA was isolated from the Wil-2 cell line by the guanidinium method and enriched for the polyadenylated (poly-A) fraction with an oligo(dT)-cellulose column (49). cDNA was made from the poly-A enriched fraction with the cDNA Synthesis System (Bethesda Research Laboratories (BRL), Gaithersburg, Md.). The cDNA was dG-tailed with dGTP and terminal transferase and ligated into similarly dC-tailed pGEM plasmid DNA with T4 DNA ligase (50). DH5 *Escherichia coli* competent cells (BRL) were transformed with the cDNA-pGEM ligation mixture and a cDNA library was constructed (49). A human hybridoma cDNA library was similarly constructed.

cDNA Isolation

The synthetic oligonucleotides were radiolabeled and hybridized with nitrocellulose filters to which the cDNA containing bacterial colonies had been fixed (49). A single colony containing a 1.2 kilobase (kb) cDNA insert was isolated. Later this 1.2 kb cDNA was radiolabeled and used to screen a human hybridoma cell cDNA library, in which a single 1.9 kb cDNA was isolated.

cDNA Characterization

Restriction enzyme analysis: The 1.2 kb cDNA was digested with various restriction enzymes and the restriction fragments were analyzed by Southern filter hybridization with the radiolabeled synthetic oligonucleotides (50).

Sequencing: Several of the cDNA restriction fragments were electroeluted from a 1% agarose-gel and subcloned into M13mp18 and M13mp19 plasmid vectors (Berhinger Mannheim Biochemicals) and single stranded DNA complementary to both strands of cDNA was produced (51). This DNA was sequenced by the Sanger dideoxy method with 35S ATP and Sequenase according to the manufacturer's recommendations (United States Biochemical corp., Cleveland, Ohio).

Northern Filter Hybridization: Total RNA and poly-A enriched RNA from several human blood cell lines (obtained as outlined above) were electrophoresed in a 1% agarose-formaldehyde gel, electrophoretically transferred to Zeta-Probe nylon reinforced support membrane according to the manufacturer's guidelines (Bio-Rad Laboratories, Richmond, Calif.), hybridized with radiolabeled cDNA and then washed at 65 degrees Celcius in 0.24×SSC (1×SSC is 0.15M NaCl and 0.015M sodium citrate, pH 7.0) and 0.1% sodium dodecyl sulfate (SDS) (52).

Southern Filter Hybridization: 15 ug of human genomic DNA was digested with various restriction enzymes, separated by 0.6% agarose gel electrophoresis and transferred to a nitrocellulose support membrane where it was hybridized with radiolabeled cDNA. Washing was performed at 0.5× SSC, 0.1% SDS and 65 degrees Celcius (50).

Radiolabeling

Synthetic oligonucleotides were end labeled with gamma 32P ATP using T4 polynucleotide kinase (50). cDNA was radiolabeled using the heximer extention method with heximer primers (Pharmacia, Inc.), alpha 32P dCTP and E. coli DNA polymerase I (Klenow fragment) (50).

Radionucleides were obtained from New England Nuclear Corp., Boston, Mass.

Autoradiography

Filters were exposed to Kodak X-OMAT-AR film for an optimal period of time, and the film was then developed on a Konica QX-60 A film processor.

Chromosomal Localization

Somatic cell hybrid clone panels were formed by polyethylene glycol mediated fusion of human lymphocytes to Chinese hamster ovary cell lines that were defective for various DNA repair capabilities. Cytogenetic analysis was used to determine the presence or absence of human chromosomes in each of the hybrid clones so formed. However, due to frequent human chromosomal alterations in these clones, the human chromosomes were more definitively detected by analysis of isoenzyme and DNA markers (53, 54). Probes for complement component 3 (3) and low density lipoprotein receptor (LDLR) were used to identify the short arm of chromosome 19.

Computer Based Sequence Analysis

The 1.9 kb cDNA nucleic acid sequence and its encoded amino acid sequence were analyzed for homologies to other published sequences. This was done with the University of Wisconsin Computer Genetics Group's Genetics Analysis software and the FASTA/FASTP programs. The nucleic acid sequence was compared to the European Molecular Biology Lab data base-Version 13 (April 1988) and the Genebank database-Version 56 (July 1988). The protein sequence was compared to the National Biomedical Research Foundation data base-Version 13 (March 1988) (55).

RESULTS

AMINO ACID SEQUENCING and SYNTHETIC OLIGONUCLEOTIDE CONSTRUCTION

A 60 kD protein with Ro antigenic activity was isolated from the Epstein-Barr virus transformed human Wil-2 B-cell line and subjected to a limited *Staphlococcus aureus* V8 protease digestion. This produced 23 and 37 kD fragments which were identified by SDS-PAGE. The amino terminal end of each domain was sequenced and this sequence information was used to construct two non-degenerate synthetic oligonucleotides (FIG. 1) as well as two different synthetic peptides.

cDNA ISOLATION and SEQUENCE ANALYSIS

A single 1.2 kb cDNA clone was isolated from the Wil-2 cell cDNA library. This clone was characterized by restriction enzyme analysis and sequenced. The cDNA encoded the previously determined amino acid sequences but the reading frame was open to the end of the cDNA with no termination codon, indicating that the cDNA identified a 2 kb RNA species but no 1.2 kb species, confirming that the cDNA was abbreviated. A human hybridoma cDNA library was subsequently screened with the 1.2 kb cDNA and a single 1.9 kb cDNA clone was isolated and sequenced. The first 1,238 base pairs of this clone are identical to the entire sequence of the 1.2 kb clone. The 1.9 kb clone contains 1,890 base pairs which includes a single 1,251 base open reading frame beginning with an AUG start site at position 67 as part of a putative Kozar ribosomal translation initiation site and ending with the termination codon UAG (FIG. 2) (56). The sequence AUUAAA (FIG. 2) is a putative polyadenylation signal (57), but there is not a typical poly-A sequence between this signal and the end of the cDNA sequence, suggesting that this 1.9 kb cDNA may be of incomplete length.

The encoded polypeptide has a molecular weight (MW) of about 48 kD which includes a 17 amino acid hydrophobic leader segment that is not present in the purified protein. The MW of the encoded polypeptide without the leader segment is approximately 14 kD less than that of the native 60 kD protein as measured by SDS-PAGE. The amino acid sequence contained no potential sites for N-linked glycosylation and deglycosylation analysis of the purified 60 kD protein shows no evidence of N or O-linked glycosylation. A highly negatively charged region is common to these proteins and may account for an incorrect SDS-PAGE MW estimation through abberant gel migration. The calculated isoelectric point of this polypeptide was 4.14 which closely approximates the value of 4.67 measured from the native purified protein (58).

Figure 3A:
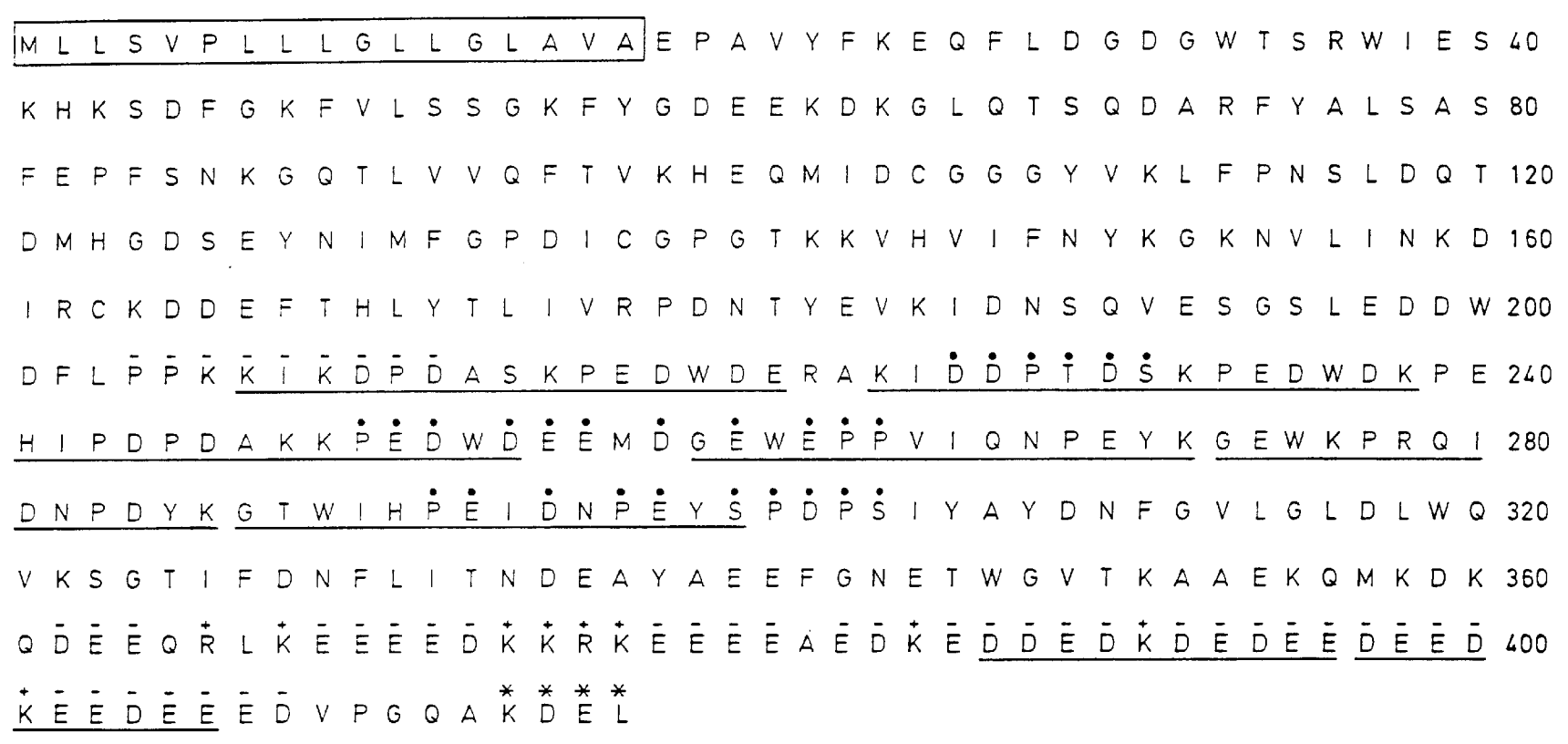

This protein contained two different sets of internal repeating sequences (FIG. 3b) which may have arisen from internal duplications and be of functional importance. The first set of duplications has 67% of its nucleic acid sequence and 73% of its amino acid sequence conserved, whereas the second set had a 60 % nucleic acid and 64% amino acid sequence conservation. This protein also contained several regions (FIG. 3a) which might allow rapid degradation as proposed by Rogers et al. for proteins containing PEST regions; regions rich in proline (P), glutamic acid (E), serine (S), and/or threonine (T) and to a lesser extent aspartic acid (D) (59).

There was no striking sequence similarity to other RNA binding proteins including another recently sequenced Ro cDNA (60 ). There was no major homology to the RNP consensus sequence (61) and no zinc finger (62) or leucine zipper (63) nucleic acid binding motifs.

A computer based analysis of the nucleic acid sequence showed no striking homology to other sequences, but the negatively charged carboxy terminus region had some minor amino acid sequence homology with a number of other proteins of diverse origin and function. The most striking of these homologies was with ubiquinone cytochrome c reductase residues 50–78, where 24 out of 29 residues were a perfect match or a Asp for Glu or Glu for Asp switch with Ro residues 385–413. The carboxy-terminal sequence Lys-Asp-Glu-Leu (KDEL) followed the negatively charged region and was identical to the carboxy signal sequence which has been shown to be crucial for the retention of several proteins in the endoplasmic reticulum (64). These other proteins also had a highly negatively charged region just proximal to the KDEL sequence. The 17 amino acid hydrophobic leader sequence was similar to that of a number of other precursor proteins and indicated that this protein may be modified in the endoplasmic reticulum (65).

Figure 4:
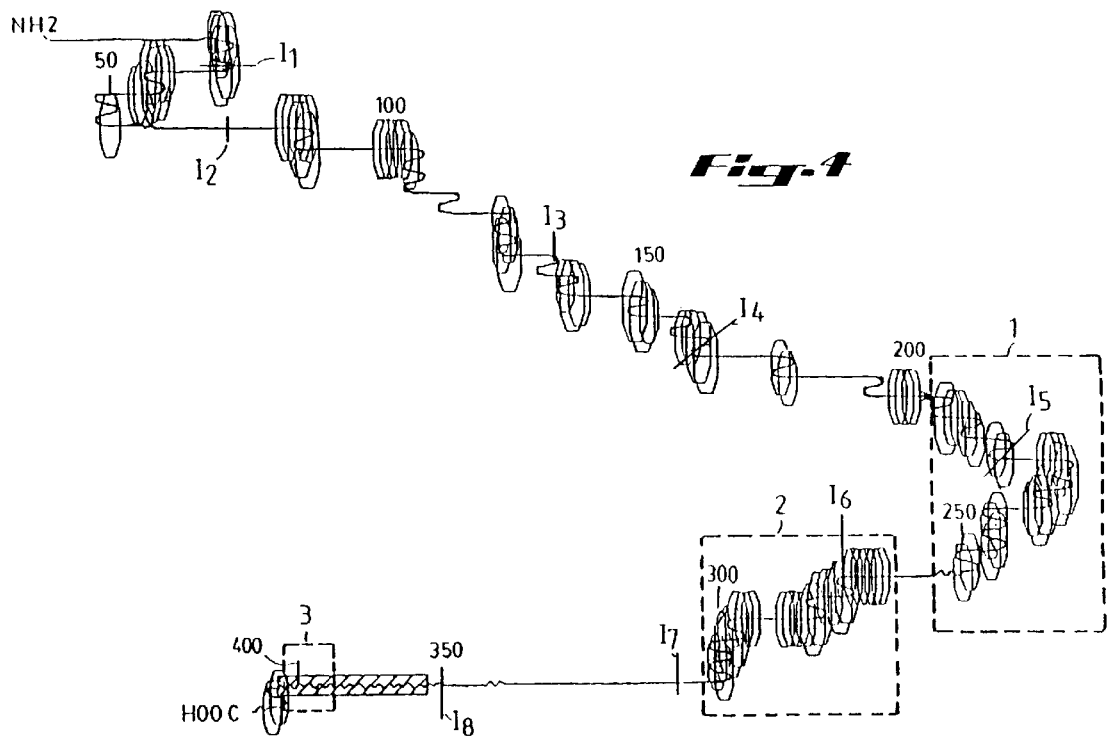
FIG. 4. Chou-Fasman structural and Jameson-Wolf antigenicity predictions of the Ro polypeptide. The numbers represent amino acid sequence positions, pleated lines represent beta sheets, wavy lines represent alpha helices and directional changes represent turns. The enclosed areas indicate potential antigenic sites. Also indicated are the positions corresponding to intron junction sites, derived from genomic mapping experiments.

Chou-Fasman secondary structure analysis predicted a complex secondary structure (FIG. 4) which included several helix-turn-helix units (centered at residues 57, 70, 210, 233 and 246), characteristic of some nucleic acid binding proteins (66). Three of these units were found within the internal duplications between residues 207 and 300 (FIG. 3), one unit per duplication. There were also several beta sheet-rich areas between residues 1–17, 144–186 186 and 285–333. The carboxy terminal residues 349–417 were predicted to have an alpha helical array.

Goldman et al. and Kyte-Doolittle hydropathic analysis predicted a strongly hydrophobic leader segment and several smaller regions of hydrophobicity, including an area-just proximal to the negatively charged carboxy terminal residues which could be a membrane spanning region. This analysis also predicted several strongly hydrophillic regions particularly between amino acids 210–300 and 350–417. The later sequence spanned the negatively charged carboxy end of the polypeptide.

Jameson-Wolf antigenicity analysis (FIG. 4) predicted the location of several potential epitopes including the previously characterized epitope at the amino terminus of this polypeptide (67,68).

SOUTHERN FILTER HYBRIDIZATION ANALYSIS and CHROMOSOMAL LOCALIZATION

Figures 3B, 5:
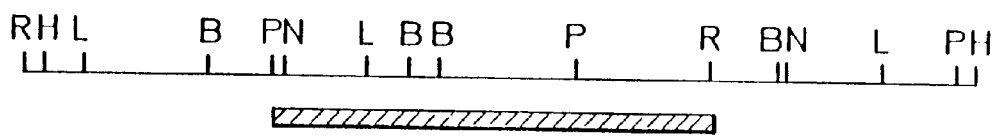
FIG. 5. Genomic restriction map. Various portions of the Ro cDNA were radiolabeled and hybridized to multiple restriction enzyme digests of human genomic DNA by the Southern technique. The length of each labeled fragment was determined and a composite restriction map was thus constructed. The map indicates that this Ro gene resides within a 6 kb stretch of chromosomal DNA.

Southern filter hybridization of Eco R1 digested genomic DNA from ten normal individuals showed a single 13.5 kb hybridizing fragment. Several other restriction enzyme digests were similarly analyzed, with the pattern of bands showing no difference between individuals, suggesting that the gene is not highly polymorphic and exists as a single copy. A similar analysis using several different radiolabeled portions of the 1.9 kb cDNA allowed the construction of a genomic restriction map as shown in FIG. 5. This Ro gene occupied approximately 6 kb of genomic DNA indicating that introns may account for about 4 kilobases of this gene.

Figure 6:
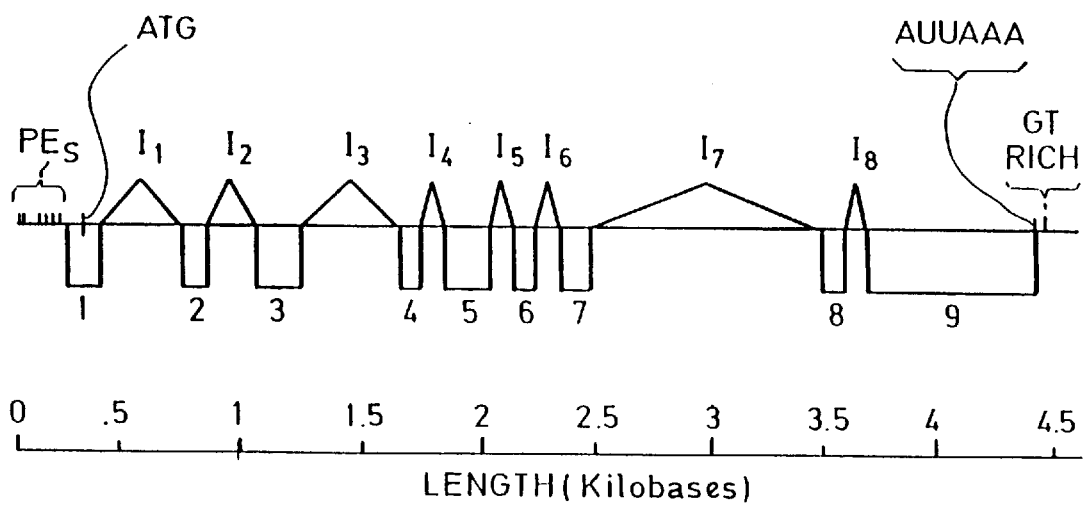
FIG. 6. Depicted is the genomic configuration of the 60 kD Ro antigen gene, showing its exons and introns in terms of relative length. Also depicted are the locations of promoter elements (PEs), poly A$^+$adenylation site (AUUAAA) and GT rich sites along the genomic sequence.
Figure 7:
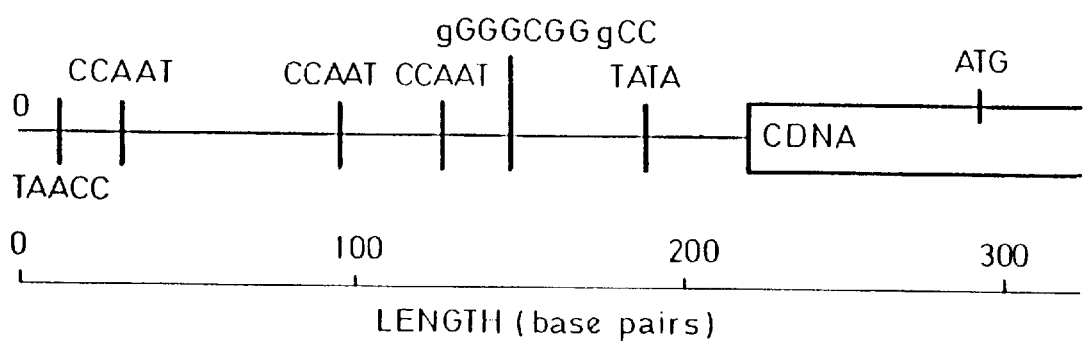
FIG. 7. Promoter elements of the 60 kD Ro antigen gene.

Depicted in FIG. 6 is a genomic intron/exon map of the 60 kD Ro antigen gene, showing the relative location and size of introns 1–8 ($I_1$–$I_8$), exons 1–9, gene regulatory promoter elements ("PEs"), and a polyadenylation site ("AUUAAA"). Shown in FIG. 7 is the relative location of various of the 60 kD Ro antigen gene promoter elements, including "GC" and "TATA" and "CCAAT" sequences. The relative position of the promoter elements with respect to the "ATG" start codon is also shown. Table VI below characterizes the exons and introns of the Ro antigen gene in some particular detail, including some comparisons to consensus exon/intron sequences. The information shown in FIGS. 6 and 7 was derived from mapping/sequencing experiments involving the Ro cDNA and genomic DNA.

TABLE VI

Ro/SS-A EXONS and INTRONS

| Exon #, size(bp) | Intron #, size(bp), type * | Consensus sequence** |
|---|---|---|
| 1 (156) | 1 (364), I | A6:GTAACG, (P)7/10 TTAG:A |
| 2 (102) | 2 (184), I | AG:GTAAGA, (P)8/10 TCAG:G |
| 3 (204) | 3 (421), I | TG:GTGAGA, (P)7/10 CTAG:G |
| 4 (95) | 4 (95), 0 | AG:GTGTGC, (P)10/10 TCAG:G |
| 5 (210) | 5 (88), 0 | AG:GTTGGT, (P)8/10 CCAG:G |
| 6 (114) | 6 (90), 0 | AG:GTGAGT, (P)10/10 GCAG:G |
| 7 (144) | 7 (¯1,000), 0 | AG:GTGAGA, (P)8/10 CCAG:G |
| 8 (84) | 8 (82), 0 | AG:GTGAGG, (P)8/10 GCAG:G |
| 9 (767, through poly A signal sequence) | | |

*Intron type 0 interrupts exons between codons, type I interrupts after first base of codon, type II interrupts after second base of codon. 54% of mammalian genes are type 0, 27% are type I, and 18% are type II. 63% of the above 8 introns are type 0 and 37% are type I.
**Vertebrate Exon/Intron Consensus sequence:
A(62%) G(77%) : G(100%) T(100%) A(60%) A(70%)
G(84%) T(50%), (P)¯8/10 N C(78%) A(100%) G(100%) :
G (55%), where N = any base The Ro cDNA was used for chromosome location by Southern filter hybridization analysis of Hind III digested DNA extracted from 38 independently derived human x Chinese hamster ovary (CHO) somatic cell hybrids that had randomly segregated human chromosomes. Ro cDNA hybridized to both human and CHO DNA fragments and the resolvable difference in fragment size (human at 19–20 kb and CHO at 5.7 kb) made it easy to determine the presence or absence of human genomic DNA among the hybrid clones. The low discordancy between Ro-hybridizing human sequences and human chromosome 19 (8S) and the apparent random association between Ro-hybridizing human sequences and every other human chromosome (34%–67% discordancy) suggested a chromosome 19 location of this gene.

The markers used to determine the presence or absence of human chromosome 19 in the hybrids (PEPD and GPI) were both located on the long arm of this small, slightly submetacentric chromosome. Therefore, the three clones (1HL14, 9HL9, and 24HL8) discordant for the chromosome 19 markers and Ro suggest that Ro might be on the short arm of the chromosome. This hypothesis was tested by examining those three hybrids for the presence of known chromosome 19 short arm markers, C3 and LDLR. The results indicated that Ro was perfectly concordant with LDLR in this set, clearly placing the gene on the short arm of chromosome 19. The discordance of LDLR with C3-PEPD-GPI in 24HL8 is consistent with, and therefore gives hybrid clone data to support, the linkage data placing LDLR distal to C3.

DISCUSSION

The above-described cDNA clone encoded a Ro RNP autoantigen, a conclusion supported by the fact that the encoded polypeptide included an amino acid sequence shown to contain a major Ro epitope (see Example I). Not all Ro antisera, as defined by conventional immunodiffusion assays, are reactive to this epitope, however (67,68). It now appears that there are multiple Ro epitopes some of which may be common to several Ro autoantigens whereas others may be unique to specific Ro autoantigens. Ro antisera are heterogeneous in recognizing one or more if the different epitopes (69,70). Whether or not certain patients with Ro antibodies can be clinically categorized by which epitopes their sera recognizes and whether or not this is related to their HLA type has yet to be determined. The ability to categorize patients based on Ro epitope recognition could have great clinical utility if the patients clinical course and/or response to therapy could be predicted by these results.

The molecular weight disparity between that measured by SDS-PAGE and that calculated from the encoded polypeptide is not difficult to reconcile in light of similar discrepancies reported with a number of other proteins, which have a very negatively charged region similar to this Ro polypeptide. This negatively charged region apparently is responsible for the retarded gel migration observed with these proteins.

The absence of a typical poly-A tail at the 3' end of the 1.9 kb cDNA shown in FIG. 2 suggests that, although it contain the entire coding region, it may be truncated in its 3' non-coding sequences. This may have arisen from aberrant cDNA synthesis or from subsequent deletion of the poly-A tail after cDNA synthesis. Another explanation would be that the Ro mRNA is not poly-A tailed, like histone mRNA. However, there is no comparable 3' end processing signal sequence as found in the histones and the 1.9 kb clone does have a poly-A signal sequence.

No major similarities were found between the RNP consensus sequence and the encoded amino acid sequence of our cDNA (61). However., the RNP consensus sequence is not necessarily a requirement nor a universal property of RNA binding proteins for it is absent in ribosomal proteins, in many viral RNA-binding nucleocapsid proteins and in the Sm-D RNP autoantigen (71,72). The three duplications between residues 207–255 have a helix-turn-helix configuration characteristic of some nucleic acid binding domains and may be a site of RNA binding. It is also of note that some viral nucleocapsid and envelop proteins have a limited sequence homology to this stretch of internal duplications as determined by computer based protein sequence analysis.

The hydrophobic leader segment of the Ro 60 kD polypeptide suggests that this protein undergoes transmembrane transport. This sequence may serve to transport this protein across the endoplasmic reticulum for modification, however there is no evidence of glycosylation. The KDEL carboxy signal sequence suggests that this protein may reside in the endoplasmic reticulum. However, indirect immunofluorescence microscopy on cultured fibroblasts and Wil-2 cells with human Ro antisera, which has been shown to react with this polypeptide, reveals predominantly intranuclear particulate staining and the polypeptide contains the sequence PPKKIKDPD (residues 203–212 in FIG. 2) which is very similar to nuclear targeting signals of other nuclear proteins (62,63). This signal sequence may facilitate transport of this protein into the nucleus.

There has been mounting evidence to support a role of foreign antigens in triggering an inappropriate immune response against self-antigens through molecular mimicry (73). An initial computer search for sequence homology to microbial agents has not been fruitful. As the Ro epitopes become better defined it may become more apparent whether microbial agents play a role in the pathogenesis of this autoimmune response.

The relationship between this Ro protein and the others is unknown. Whether they are structurally or functionally related has not been determined and the RNA binding properties of each of the Ro proteins has not been well defined. Ro antisera specific for a 52 kD or a 60 kD protein have been shown to immunoprecipitate the hY RNAs from cellular extracts (70). Protein binding to a hY RNA has also been demonstrated in reconstitution studies with another recently characterized 60 kD Ro RNP, through the efficiency of reconstitution was reportedly quite low (60).

Now that several different proteins with Ro antigenicity have been identified, including another 60 kD protein which appears to bind hY RNA, the term Ro (or SS-A) should probably not be used exclusively for any one of these proteins. However, to avoid confusion with existing nomenclature the present inventors have continued to refer to the 60 kD antigen of the present invention as the "60 kD Ro antigen". Yet, as each of these Ro autoantigens are further characterized, a system of classification should evolve so that each gets a more unique designation. The characterization of the various Ro cDNAs and their encoded epitopes should be helpful in this regard and also provide a means to further clarify the functional and pathologic roles of these protein autoantigens.

It will be apparent to those of skill in the art that numerous modifications and changes may be made in the present invention in light of the present disclosure without departing from the spirit and scope of the invention. For example, it will be apparent in light of the present disclosure that numerous approaches can be taken in expression of the 60 kD Ro coding sequences, or subfragments thereof, to produce the 60 kD protein or antigenic fragments. Similarly, for example, in connection with immunoassays, although the present inventors have chosen the ELISA system with a peroxidase enzyme tag, there is no reason why other systems such as an RIA-based immunoassay system, or the use of different enzymes, such as alkaline phosphatase, urease or even DNA capture, cannot be used with equal utility. Numerous other changes will be equally apparent. It is intended that all such changes be within the spirit and scope of the claims which follow.

REFERENCES (1) Bernstein et al. (1987), *J. Rheumatol.*, 14 (Supp. 13):83–88.

(2) Sontheimer et al. (1978), *J. Lab. Clin. Med.*, 91:550–558.

(3) Koffler et al. (1971), *J. Exp. Med.*, 134:294.

(4) Schur et al. (1968), *N. Engl. J. Med.*, 278:533.

(5) Tan et al. (1966), *J. Immunol.*, 96:464.

(6) Koffler et al. (1967), *J. Exp. Med.*, 126:607.

(7) Rubin et al. (1982), *Arth. Rheum.*, 25:779–782.

(8) Aitkaci et al. (1981), *J. Immunol. Meth.*, 44:311–322.

(9) Gioud et al. (1982), *Arth. Rheum.*, 25:407–413.

(10) Jones, B. R. (1958), *Lancet*, 2:773–776.

(11) Anderson et al. (1961), *Lancet*, 2:456–460.

(12) Reichlin, M. (1986), *J. Clin. Immunol.*, 6:339–348.

(13) Reichlin et al. (1987), *J. Rheumol.*, 14 (Supp. 13):112–117.

(14) Harley et al. (1986), *Arth. Rheum.,* 29:196–206.
(15) Lieu et al. (1984), *Jrnl. Immunol. Meth.,* 71:217–228.
(16) Kyte et al. (1982), *J. Mol. Biol.,* 157:105.
(17) Lieu et al. (1984), *J. Immunol. Meth.,* 71:217–228.
(18) Geyson et al. (1987), *Science,* 235:1184–1190.
(19) Chambers et al. (1985), *Proc. Natl. Acad. Sci. USA,* 82:2115–2119.
(20) Bruist et al. (1987), *Science,* 235:777–780.
(21) Bixler et al. (1986), *Biochem. J.,* 240:139–146.
(22) Watts et al. (1985), *Proc. Natl. Acad. Sci. USA,* 82:5480–5484.
(23) Kazim et al. (1982), *Biochem. J.,* 191:261–264.
(24) Kazim et al. (1982), *Biochem. J.,* 203:201–208.
(25) Buus et al. (1987), *Science,* 235:1191–1196.
(26) Getzoff et al. (1987), *Science,* 235:1191–1196.
(27) Mamula et al. (1986), *J. Exp. Med.,* 86:1889–1901.
(28) Adelman et al., (1983), DNA, 2:183.
(29) Messing et al. (1981), Third Cleveland Symposium on Macromolecules and Recombinant DNA, Editor A. Walton, Elsevier, Amsterdam.
(30) Crea et al. (1978) Proc. Natl. Acad. Sci. U.S.A., 75:5765.
(31) Bolivar et al. (1977), Gene, 2:95.
(32) Chang et al. (1978), Nature, 375:615.
(33) Itakura et al. (1977), Science, 198:1056.
(34) Goeddel et al. (1979), Nature, 281:544.
(35) Goeddel et al. (1980), Nucleic Acids Res., 8:4057.
(36) EPO Appl. Publ. No. 0036776.
(37) Stinchcomb et al. (1979), Nature, 282:39.
(38) Kingsman et al. (1979), Gene, 7:141.
(39) Tschemper et al. (1980), Gene, 10:157.
(40) Jones (1977), Genetics, 85:12.
(41) Hitzeman et al. (1980), J. Biol. Chem., 255:2073.
(42) Hess et al. (1968), J. Adv. Enzyme Reg., 7:149.
(43) Holland et al. (1978), Biochemistry, 17:4900.
(44) *Tissue Culture,* Academic Press, Kruse and Patterson, editors (1973).
(45) Fiers et al. (1978), Nature, 273:113.
(46) Lieu et al. (1988), J. Clin. Invest., 82:96–101.
(47) Darbre (1986) ed. Practical Protein Chemistry 0 A Handbook. New York: John Wiley and Sons.
(48) Lathe (1985), J. Mol. Biol., 183:1–12.
(49) Maniatis et al. (1982), Molecular Cloning—A Laboratory Manual. Cold Spring Harbor Laboratory, Cold Spring Harbor, N.Y.
(50) Ausubel et al. (1987), Current Protocols in Molecular Biology. New York: John Wiley and Sons.
(51) Yanisch-Perron et al. (1985), Gene, 33:103–119.
(52) Zeta-Probe Blotting Membranes. (1985) Bio-Rad bulletin 1110. Bio-Rad Laboratories, Richmond, Calif.
(53) Stallings et al. (1988), Am. J. Hum. Genet., 43:144–151.
(54) McBride et al. (1987), Proc. Natl. Acad. Scd., 84:503–507
(55) Devereux et al. (1984), NAR, 12:387–395.
(56) Kozak (1986), Cell, 44:283–292.
(57) Nevins (1983), *Ann. Rev. Biochem.,* 52:441–66.
(58) Lieu et al. (1984), J. Immunol. Methods, 71:217–228.
(59) Rogers et al. (1986), Science, 234:364–368.
(60) Deutscher et al. (1988), Proc. Natl. Acad. Sci., 85:9479–9483.
(61) Adam et al. (1986), Mol. Cell. Biol., 6:2932–2943.
(62) Evans et al. (1988), Cell, 52:1–3.
(63) Landschulz et al. (1988), Science, 240:1759–1764.
(64) Munro et al. (1987), Cell, 48:899–907.
(65) Walter et al. (1984), Cell, 38:5–8.
(66) Berg (1986), Nature, 319:264–265.
(67) Lieu et al. (1989), Journal of Autoimmunity. In press
(68) Lieu et al. Epitope mapping of the human Wil-2 cell Ro/SS-A (Ro) autoantigenic polypeptide. (abstract) Submitted.
(69) Radar et al. (1989), J. Clin. Invest. In press
(70) Ben-Chetrit et al. (1988), J. Exp. Med., 167:1560–1571.
(71) Swanson et al. (1987), Mol. Cell. Biol., 7:1731–1739.
(72) Rokeach et al. (1988), Proc. Natl. Acad. Sci., 85:4832–4836.
(73) Oldstone (1987), Cell, 50:819–820.
(74) Tabor et al. (1985), *Proc. Natl. Acad. Sci. USA,* 82:1074–8
(75) Miyamoto et al. (1985), *Mol. Cell. Biol.,* 5:2860–5.
(76) Andrews et al. (1988), *Biochem. J.,* 252:199–206

What is claimed is:

1. A purified nucleic acid segment that encodes an amino acid sequence as set forth in FIG. 2 of the drawings.

2. A purified nucleic acid segment that corresponds to, or is complementary to, from a 14 to 1890 nucleotide long region of the DNA sequence of FIG. 2 of the drawings, said segment being capable of forming a hybrid with the nucleotide sequence of FIG. 2 under conditions that include 6×SSC at 42° C.

3. The nucleic acid segment of claim 2, wherein the segment corresponds to, or is complementary to, from an 18 to 1890 nucleotide long region of the DNA sequence of FIG. 2 of the drawings.

4. The nucleic acid segment of claim 2, wherein the segment corresponds to, or is complementary to, from a 22 to 1890 nucleotide long region of the DNA sequence of FIG. 2 of the drawings.

5. A purified nucleic acid segment that encodes a peptide having the amino acid sequence phe-lys-glu-gln-phe-leu-asp-gly-asp-gly-trp-thr-asp-arg or lys-glu-gln-phe-leu-asp-gly-asp-gly-trp-thr-asp-arg-trp-ile-glu-ser.

6. A recombinant vector comprising a nucleic acid segment that:
 (a) encodes an amino acid sequence as set forth in FIG. 2 of the drawing;
 (b) encodes the amino acid sequence phe-lys-glu-gln-phe-leu-asp-gly-asp-gly-trp-thr-asp-arg;
 (c) encodes the amino acid sequence lys-glu-gln-phe-leu-asp-gly-asp-gly-trp-thr-asp-arg-trp-ile-glu-ser; or
 (d) that corresponds to, or is complementary to, from a 14 to 1890 nucleotide long region of the DNA sequence of FIG. 2 of the drawings, said segment being capable of forming a hybrid with the nucleotide sequence of FIG. 2 under conditions that include 6×SSC at 42° C.

7. The recombinant vector of claim 6, further defined as encoding an amino acid sequence as set forth in FIG. 2 of the drawing.

8. The recombinant vector of claim 6, further defined as encoding an amino acid sequence phe-lys-glu-gln-phe-leu-asp-gly-asp-gly-trp-thr-asp-arg.

9. The recombinant vector of claim 6, further defined as encoding an amino acid sequence lys-glu-gln-phe-leu-asp-gly-asp-gly-trp-thr-asp-arg-trp-ile-glu-ser.

10. The recombinant vector of claim 6, further defined as comprising a segment that corresponds to, or is complementary to, from a 14 to 1890 nucleotide long region of the DNA sequence of FIG. 2 of the drawings, said segment being capable of forming a hybrid with the nucleotide sequence of FIG. 2 under conditions that include 6×SSC at 42° C.

11. A method for the expression of an antigen comprising the steps of:
   (a) obtaining a nucleic acid segment as defined by any one of claims 1, 5, or 7–9 and
   (b) expressing the antigen encoded by the segment in an appropriate host.

12. A method for identifying the presence of a nucleic acid molecule having a sequence in accordance with any one of claims 2 through 4 in a biological sample suspected of containing such a molecule, the method comprising the steps of:
   (a) incubating nucleic acids from the biological sample with a DNA segment as defined by any one of claims 2 through 4 under conditions appropriate for the formation of specific hybrids; and
   (b) detecting the formation of specific hybrids between the nucleic acids and the segment by means of a detectable label, the formations of such hybrids being indicative of the presence of such a nucleic acid sequence in the biological sample.

13. The method of claim 12 wherein the biological sample comprises a recombinant host cell colony.

14. The method of claim 12 wherein the biological sample comprises isolated DNA.

15. A method of testing for the presence of anti-Ro antibodies in a sample, the method comprising the steps of:
   (a) preparing an antigen in accordance with claim 12; and
   (b) immunologically testing the sample for antibodies which cross react with the antigen.

* * * * *

UNITED STATES PATENT AND TRADEMARK OFFICE
CERTIFICATE OF CORRECTION

PATENT NO.    : 6,303,339 B1
DATED         : January 8, 2002
INVENTOR(S)   : Sontheimer et al.

It is certified that error appears in the above-identified patent and that said Letters Patent is hereby corrected as shown below:

<u>Drawings,</u>
FIG.1, please delete "polypetide" and insert -- polypeptide -- therefor.

<u>Column 32,</u>
Line 16, please delete "12" and insert -- 11 -- therefor.

Signed and Sealed this

Twenty-seventh Day of August, 2002

Attest:

JAMES E. ROGAN
Attesting Officer     Director of the United States Patent and Trademark Office